United States Patent
Thaker et al.

(10) Patent No.: US 11,802,883 B2
(45) Date of Patent: Oct. 31, 2023

(54) SYSTEMS AND METHODS FOR OPTIMIZING AN INSTRUMENT SYSTEM WORKFLOW

(71) Applicant: Berkeley Lights, Inc., Emeryville, CA (US)

(72) Inventors: Darshan Thaker, Oakland, CA (US); Matthew E. Fowler, Oakland, CA (US); Samira A. Nedungadi, Oakland, CA (US); Daniel A. Banda Villanueva, Oakland, CA (US); Brandon R. Bruhn, Berkeley, CA (US); Nenad Bozinovic, San Francisco, CA (US); Kellen C. Mobilia, Dublin, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 351 days.

(21) Appl. No.: 16/882,331

(22) Filed: May 22, 2020

(65) Prior Publication Data

US 2020/0371126 A1    Nov. 26, 2020

Related U.S. Application Data

(60) Provisional application No. 62/852,955, filed on May 24, 2019.

(51) Int. Cl.
*G01N 35/00* (2006.01)
*G06N 20/00* (2019.01)

(52) U.S. Cl.
CPC . *G01N 35/00623* (2013.01); *G01N 35/00693* (2013.01); *G01N 35/00871* (2013.01);
(Continued)

(58) Field of Classification Search
CPC ... G01N 2035/00881; G01N 2035/009; G01N 2035/0091; G01N 35/00623;
(Continued)

(56) References Cited

U.S. PATENT DOCUMENTS

| 2011/0282188 A1 | 11/2011 | Burnside et al. |
| 2012/0207365 A1 | 8/2012 | Verstraeten et al. |

(Continued)

FOREIGN PATENT DOCUMENTS

| CA | 2338246 A1 | 2/2000 |

OTHER PUBLICATIONS

Supplementary European Search Report for Application No. 201815339.

*Primary Examiner* — Tri T Ton
(74) *Attorney, Agent, or Firm* — InventIQ Legal LLP; Anna Ison; Daniel J. Kennedy

(57) ABSTRACT

A system and a method for dynamically optimizing an instrument system workflow based on operational monitoring and managing of a workflow for a hardware system. The system includes instrument resources and sample chambers, each resource and chamber with a dedicated sensor configured to acquire data. The system further includes a computing device communicatively connected to the instrument resources and sample chambers. The computing device includes a software application or program comprising a workflow builder, an execution engine, an analytics engine, a virtual system modeling engine, and an optional machine learning engine.

22 Claims, 21 Drawing Sheets

(52) U.S. Cl.
CPC ....... *G06N 20/00* (2019.01); *G01N 2035/009* (2013.01); *G01N 2035/0091* (2013.01)

(58) Field of Classification Search
CPC ....... G01N 35/00693; G01N 35/00871; G01N 35/0092; G06N 20/00
USPC ......................................................... 702/122
See application file for complete search history.

(56) References Cited

U.S. PATENT DOCUMENTS

| | | |
|---|---|---|
| 2012/0304096 A1 | 11/2012 | Shikhman |
| 2013/0205240 A1 | 8/2013 | Ling et al. |
| 2014/0222521 A1 | 8/2014 | Chait |
| 2014/0342465 A1 | 11/2014 | Haechler et al. |
| 2017/0021356 A1 | 1/2017 | Cepheid |
| 2017/0161130 A1 | 6/2017 | Goldstein et al. |
| 2017/0193167 A1 | 7/2017 | Wood et al. |
| 2018/0005149 A1 | 1/2018 | Dhingra |

Figure 14G

SYSTEMS AND METHODS FOR OPTIMIZING AN INSTRUMENT SYSTEM WORKFLOW

RELATED APPLICATIONS

The present application claims priority to and the benefit of U.S. Provisional Patent Application No. 62/852,955, entitled "SYSTEMS AND METHODS FOR OPTIMIZING AN INSTRUMENT SYSTEM WORKFLOW" and filed on May 24, 2019, the entire contents of which are hereby incorporated by reference for all purposes.

FIELD

The disclosure described herein relates generally to a system and a method for managing a workflow, and more particularly, relates to optimizing an instrument workflow program via system monitoring, dynamic implementation of a series of operations in an instrument system.

BACKGROUND

A computer program or a software application that runs on a computing device can be used to manage a physical apparatus or a hardware system, such as an instrument system. Generally, a hardware system, which may include various functional components and tools, can be controlled and managed by the software application specifically designed to execute certain functions of the hardware system. The software application specifically created for that particular hardware system often includes a workflow for executing specific functions of the hardware system, and the functions are often precisely programmed for the application. Since the software application is created to provide a specific set of instructions in the pre-programmed workflow, it is seldom optimized and typically not altered or adjusted during the operation. Therefore, an improved approach is needed for dynamically managing a hardware system so as to optimize the workflows that are executed by the system.

SUMMARY

At least one aspect is directed to a system for dynamically optimizing an instrument system workflow. The system includes one or more instrument resources, and one or more instrument resource sensors configured to acquire data from the one or more instrument resources. Each resource can have, for example, a dedicated instrument resource sensor configured to acquire data from its corresponding instrument resource. The system also includes one or more sample chambers, and one or more sample chamber sensors. Each sample chamber can have, for example, a dedicated sample chamber sensor configured to acquire data from its corresponding sample chamber. The system further includes a computing device communicatively connected to the one or more instrument resource sensors and one or more sample chamber sensors. In various embodiments, data (including sensor data and user input) can be acquired in real-time. In various embodiments, data (including sensor data and user input) can be acquired periodically according pre-set time intervals.

In various implementations of the system, the computing device includes a workflow builder configured to allow a user to create an instrument workflow program for an instrument system. In various implementations of the system, the computing device also includes a virtual system modeling engine configured to optimize the instrument workflow program utilizing a virtual system model of the instrument system and generate an optimized instrument workflow program. In various implementations of the system, the computing device further includes an analytics engine communicatively connected to the dedicated instrument resource sensors and sample chamber sensors, the analytics engine configured to monitor data output from the sensors, initiate a calibration operation to update the virtual system model and, as needed, re-optimize the instrument workflow program when a variance condition is detected in the data output from the sensors. In various implementations of the system, the computing device also includes an execution engine configured to process the optimized (or re-optimized) instrument workflow program for the instrument system and provide operating instructions to the one or more instrument resources and sample chambers.

In various implementations of the system, the computing device also includes a machine learning engine configured to train the analytics engine to further improve the optimized instrument workflow program.

In various implementations, the one or more instrument resources comprises a pump, a nest, a needle, or a receptacle. In various implementations, the one or more sample chambers comprises an incubator, a well plate, and/or a sample tube.

In various implementations, the one or more instrument resources and the one or more sample chambers are housed within a housing. In various implementations, the one or more instrument resource sensors, the one or more sample chamber sensors, and/or the computing device are also housed within the housing. In various implementations, the variance condition includes an alarm from at least one of the sensors, a warning of low material detected by the sensors, a result of a periodic image analysis, or an end of workflow step notification.

At least one aspect is directed to a method for dynamically optimizing an instrument system workflow comprising one or more operating instructions for an instrument resource and a sample chamber. The instrument resource and the sample chamber may be housed in an instrument system. The method can optionally include creating the instrument workflow program, e.g., based on user input. The method includes acquiring data from sensors monitoring the instrument resource and sample chamber and, optionally, user input. The method also includes creating a virtual system model of the instrument system and updating the virtual system model in response to detecting a variance condition in the acquired data. The virtual system model can be based, at least in part, on requirements of the instrument system workflow. The method further includes generating an optimized instrument workflow program utilizing the virtual system model and, as needed, generating a re-optimized instrument workflow program utilizing an updated virtual system model. The method also includes providing operating instructions to the instrument resource and sample chamber based on the optimized (or re-optimized) instrument workflow program. In various embodiments, the data can be acquired in real-time. In various embodiments, the data can be acquired periodically according pre-set time intervals.

In various implementations, the method further includes improving the virtual system model utilizing machine learning and generating a further optimized instrument workflow program utilizing the improved virtual system model. In various embodiments, the improved virtual system model is updated in response to detecting a variance condition in the acquired data and, as needed, a re-optimized instrument workflow program is generated using the updated and improved virtual system model.

In various implementations of the method, the instrument resource comprises a pump, a nest, a needle, or a receptacle. In various implementations of the method, the sample chamber comprises an incubator, a well plate, and/or a sample tube.

In various implementations of the method, the instrument resource (or sensor thereof) and the sample chamber (or sensor thereof) are communicatively coupled to a computer device via a network connection. In various implementations of the method, the instrument system comprises a computing device that is communicatively coupled to the instrument resource (or sensor thereof) and the sample chamber (or sensor thereof).

In various implementations of the method, updating the virtual system model includes updating periodically at a preset interval. In various implementations of the method, the variance condition includes an alarm from one or more of the sensors, a warning of low material detected by one or more of the sensors, a result of a periodic image analysis, or an end of workflow step notification.

At least one aspect is directed to a non-transitory machine-readable storage medium comprising machine-readable instructions for causing a processor to execute a method for dynamically optimizing an instrument system workflow comprising one or more operating instructions for an instrument resource and a sample chamber. The instrument resource and the sample chamber may be housed in an instrument system. The machine-readable instructions can optionally facilitate creation of the instrument system workflow, e.g., based on user input. The machine-readable instructions include acquiring data from sensors monitoring the instrument resource and sample chamber and, optionally, user input. The machine-readable instructions also include creating a virtual system model of the instrument system and updating, as needed, the virtual system model in response to detecting a variance condition in the acquired data. The virtual system model can be based, at least in part, on requirements of the instrument system workflow. The machine-readable instructions further include generating an optimized instrument workflow program utilizing the virtual system model and, as needed, generating a re-optimized instrument workflow program utilizing an updated virtual system model. The machine-readable instructions also include providing operating instructions to the instrument resource and sample chamber based on the optimized (or re-optimized) instrument workflow program. In various embodiments, the data can be acquired in real-time. In various embodiments, the data can be acquired periodically according pre-set time intervals.

In various implementations of the non-transitory machine-readable storage medium, the method further includes improving the virtual system model utilizing machine learning and generating a further optimized instrument workflow program utilizing the improved virtual system model. In various embodiments of the methods executed by the non-transitory machine-readable storage medium, the improved virtual system model is updated in response to detecting a variance condition in the acquired data and, as needed, a re-optimized instrument workflow program is generated using the updated and improved virtual system model.

In various implementations of the methods executed by the non-transitory machine-readable storage medium, the instrument resource comprises a pump, a nest, a needle, or a receptacle. In various implementations of the methods executed by the non-transitory machine-readable storage medium, the sample chamber comprises an incubator, a well plate, and/or a sample tube.

In various implementations of the methods executed by the non-transitory machine-readable storage medium, the instrument resource (or sensor thereof) and the sample chamber (or sensor thereof) are communicatively coupled to a computer device via a network connection. In various implementations of the methods executed by the non-transitory machine-readable storage medium, the instrument system comprises a computing device that is communicatively coupled to the instrument resource (or sensor thereof) and the sample chamber (or sensor thereof).

In various implementations of the methods executed by the non-transitory machine-readable storage medium, updating the virtual system model includes updating periodically at a preset interval. In various implementations of the methods executed by the non-transitory machine-readable storage medium, the variance condition includes an alarm from one or more of the sensors, a warning of low material detected by one or more of the sensors, a result of a periodic image analysis, or an end of workflow step notification.

At least one aspect is directed to a system for dynamically optimizing an instrument workflow. The system includes one or more instrument resources, one or more instrument resource sensors, a holder for a sample chamber, one or more sample chamber sensors, one or more receptacles, and a computing device. The instrument resource sensors are configured to acquire data from the instrument resources. The receptacles are configured to hold a reagent. The computing device is communicatively connected to the instrument resources/sensors and the sample chamber resources/sensors. The computing device is comprised of a workflow builder, an operation framework, a set of operations, and a workflow modeling component.

In various implementations of the system, the workflow builder is configured to accept user input and create a workflow program to be performed by the instrument system, wherein the workflow program is comprised of a series of operations. Each operation of the series of operations can be selected and/or configured by the user.

In various implementations of the system, the operations framework is configured to direct the performance of the workflow program by the instrument system by calling each operation in the series of operations, wherein timing of the calling of operations is adjusted based on data received from the one or more instrument resource sensor, the one or more sample chamber sensors, at least one operation, and/or additional user input, to thereby optimize time to completion of the workflow program.

In various implementations of the system, each operation of the set of operations is configured to instruct one or more instrument resources to perform a predetermined task.

In various implementations of the system, the workflow modeling component is configured to receive data from the operations framework and, optionally, the operations in the series of operations, and maintain a model of the status of the workflow program based upon the received data.

At least one aspect is directed to a method for dynamically optimizing a workflow program, the workflow program comprising a series of operations, each operation of the series comprising operating instructions for one or more instrument resources housed in an instrument system. Data is acquired from sensors monitoring the one or more instrument resources and a sample chamber comprising a sample. The workflow program is optimized in response to detecting a variance condition in the acquired data. The optimized workflow is utilized to update a model of the status of the workflow program. Operating instructions are provided to the one or more instrument resources based on the optimized instrument workflow program.

At least one aspect is directed to a non-transitory machine-readable storage medium comprising machine-readable instructions for causing a processor to execute a method for dynamically optimizing a workflow program, the workflow program comprising a series of operations, each operation comprising operating instructions for one or more instrument resources housed in an instrument system. Data is acquired from sensors monitoring the one or more instrument resources and a sample chamber comprising a sample. The workflow program is optimized in response to detecting a variance condition in the acquired data. The optimized workflow is utilized to update a model of the status of the workflow program. Operating instructions are provided to the one or more instrument resources based on the optimized instrument workflow program.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIGS. 14A to 14G are illustrations of a GUI that depicts the progress of an instrument workflow in operation, according to various embodiments.

DETAILED DESCRIPTION

Figure 1:
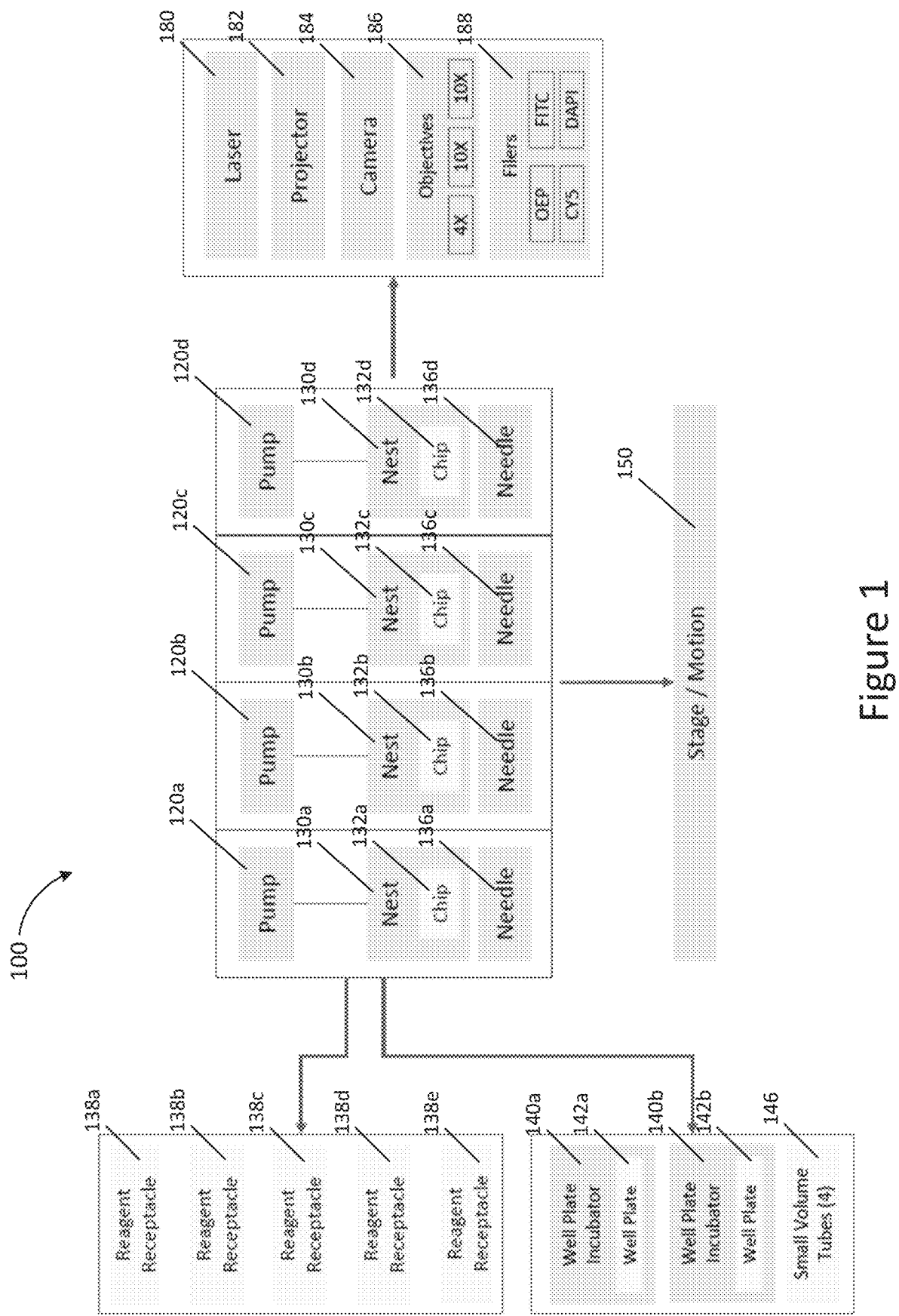
FIG. 1 shows an example instrument system, according to various embodiments.

Since a typical instrument workflow includes a particular set of executable operations by the instrument system, i.e., the order and various operations of the instrument components are pre-programmed, any adjustments or forms of alteration in the operation of the instrument system cannot be implemented, either on the fly, during operation, or in real-time. This is particularly imperative if and when a situation arises during the operation of the instrument system that requires alteration or adjustment in the execution of the pre-programmed operations (i.e., instrument workflow run). In such a situation, the system as a whole may not work efficiently and/or properly. Therefore, systems and methods that can allow an instrument workflow to be adjusted in the middle of an instrument run and can be improved to accommodate and/or implement both expected and unexpected alterations or adjustments during the instrument's operation can provide some distinct advantages over conventional systems and methods that only allow for static pre-set instrument workflow runs. That is, there is a need for operational monitoring and managing of an instrument workflow during an instrument run in order to optimize an instrument system workflow.

The disclosure as described herein includes various implementations of a system for dynamically optimizing an instrument system workflow based on operational monitoring and managing of a workflow for a hardware system, such as an instrument system. The technologies described herein include analytics and/or optimization routines that are based on sensing and implementation of optimized workflow program.

In particular, various implementations of a system for dynamically optimizing an instrument system workflow are described herein. In various implementations disclosed herein, the system includes one or more instrument resources that are being managed by the system. In each instrument resource of the one or more instrument resources, the instrument includes a dedicated instrument resource sensor that is configured to acquire data from the instrument resource. In various embodiments, the data can be acquired in real-time. In various embodiments, the data can be acquired periodically according pre-set time intervals.

In various implementations, the system also includes one or more sample chambers that are being monitored by the system. In each sample chamber of the one or more sample chambers, the chamber includes a dedicated sample chamber sensor that is configured to acquire data in the sample chamber.

In various implementations, the system also includes a computing device communicatively connected to the one or more instrument resources and the one or more sample chambers. In accordance with various implementations disclosed herein, the computing device includes a workflow builder that is configured to allow a user to create an instrument workflow program for an instrument system. The instrument workflow program is a series of instrument operations that are to be executed by the instrument system in accordance with a set order or timing interval. In various implementations, the computing device also includes a virtual system modeling engine that is configured to optimize the instrument workflow program utilizing a virtual system model of the instrument system and generate an optimized instrument workflow program. That is, an instrument workflow program that utilizes the instrument resources in as efficient (in resource time or resources) a manner as possible to service the one or more sample chambers.

In various implementations, the computing device also includes an analytics engine communicatively connected to the dedicated instrument resource sensors and the dedicated sample chamber sensors. In various implementations, the analytics engine is configured to monitor data output from the dedicated instrument resource sensors and the dedicated sample chamber sensors. In various implementations, the analytics engine is configured to initiate a calibration operation to update the virtual system model when a variance condition is detected in the data output from the sensors. Examples of a variance condition can include, but are not limited to: low or empty reagent levels, reduced or total loss of function in the operation of the sample chamber, malfunction of an instrument system component, etc.

In various implementations, the computing device also includes an execution engine that is configured to process the optimized instrument workflow program for the instrument system and provide operating instructions to the one or more instrument resources and sample chambers to execute.

The disclosure as described herein also relates to various implementations of a method for dynamically optimizing an instrument system workflow. In various implementations disclosed herein, the method includes creating an instrument workflow program that includes one or more operating instructions for an instrument system. In various implementations, the instrument system includes an instrument resource and a sample chamber housed in the instrument system. In various implementations, the method also includes acquiring data from sensors monitoring the instrument resource and sample chamber. In various implementations, the sensors are configured to acquire data in the instrument resource and the sample chamber. In various embodiments, the data can be acquired in real-time. In various embodiments, the data can be acquired periodically according pre-set time intervals.

In various implementations, the method includes updating a virtual system model of the instrument system in response to detecting a variance condition in the acquired data. In various implementations, the variance condition includes, for example, but not limited to an alarm from a malfunctioning hardware component in the system, a warning of low reagent or material levels, reduced or total loss of function in the operation of the sample chamber, and the like.

In various implementations, the method includes generating an optimized instrument workflow program utilizing the updated virtual system model, and providing operating instructions to the instrument resource and sample chamber based on the optimized instrument workflow program. An optimized instrument workflow program is one that results in the utilization of instrument resources in as efficient (in resource time or resources) a manner as possible to service the one or more sample chambers.

As used herein, a system denotes a set of components, real or abstract, comprising a whole where each component interacts with or is related to at least one other component within the whole. Examples of systems include machinery, factories, instrument systems, software applications, software programs, electrical systems, processing plants, devices, chemical processes, biological systems, data centers, and the like.

As used herein, a software application or program is a collection of instructions that performs a specific task when executed by a computing device, such as a personal computer, a portable computer, a main frame computer, a server, or a network server, etc. A software application or program can be a stand-alone application or a network application. A stand-alone application can reside on any of the aforementioned computing devices. A network application is any application that is stored on an application server connected to a network (e.g., local area network, wide area network, etc.) in accordance with any contemporary client/server architecture model and can be accessed via the network. In this arrangement, the network application programming interface (API) resides on the application server separate from an external machine. The external interface would typically be a web browser (e.g. CHROME™, SAFARI™, INTERNET EXPLORER™, FIREFOX™, etc.) that is in communication with the network application server via a network connection (e.g., HTTP, HTTPS, RSS, etc.).

The following figures and descriptions with respect to the figures provide additional details of the various implementations of the device and the methods for producing the same. Systems having components described herein, including pumps, stages, optical trains, cameras, nests that support and interface with chips, sensors, and the like, have been described, e.g., in PCT Application Nos. WO 2016/094507 and WO 2018/102747. The chips discussed herein can be, for example, microfluidic chips. Exemplary microfluidic chips have been described, e.g., in PCT Application Nos. WO 2014/070873 and WO 2015/061497. Well plate incubators have been described, for example, PCT Application Nos. WO 2017/059273 and WO 2018/102781.

FIG. 1 shows an example instrument system 100, according to an illustrative implementation. As shown in FIG. 1, the instrument system 100 includes a plurality of pumps 120a, 120b, 120c, and 120c (collectively referred to as "pumps 120"), a plurality of nests 130a, 130b, 130c, and 130d (collectively referred to as "nests 130"), a plurality of chips 132a, 132b, 132c, and 132d (collectively referred to as "chips 132") and a plurality of needles 136a, 136b, 136c, and 136d (collectively referred to as "needles 136"). As shown in FIG. 1, each of the pumps 120 are operatively coupled to one of the nests 130. For example, the pump 120a is operatively coupled to the nest 130a, the pump 120b is operatively coupled to the nest 130b, and so on. Each of the nests 130 includes a chip 132, as shown in FIG. 1. For example, the nest 130a includes the chip 132a, the nest 130b includes the chip 132b, and so on. In various implementations, each of the pumps 120 is configured to actuate one of the needles 136. For example, the pump 120a is configured to actuate the needle 136a, the pump 120b is configured to actuate the needle 136b, and so on. In other words, FIG. 1 shows the instrument system 100 that includes four sets of the pumps 120, the nests 130, the chips 132, and the needles 136, and each set is configured to function as a pumping unit. In essence, the four pumping units shown in FIG. 1 are configured to perform the same or substantially similar function.

In various implementations, each of the pumps 120, the nests 130, the chips 132, and/or the needles 136 can include a dedicated sensor configured to acquire data from the respective pump, nest, chip, and/or needle. The sensors maybe different for the different components. In various implementations, the sensor can include a sensor for monitoring, for example, pump condition, chip consumption, chip remaining, needle position, etc. In various embodiments, the data can be acquired in real-time. In various embodiments, the data can be acquired periodically according pre-set time intervals.

FIG. 1 also shows that the instrument system 100 includes a plurality of receptacles 138a, 138b, 138c, 138d, and 138e (collectively referred to as "receptacles 138"). In various implementations, the receptacles 138 can be configured to store, for example, a fluid, a reagent, a chemical solution, a buffer and any suitable liquid or powder. In various implementations, each of the receptacles 138 can include a dedicated sensor configured to acquire data from the respective receptacle. In various implementations, the sensor can include a sensor for monitoring the fluid level to provide the amount of remaining fluid in the receptacle. In various embodiments, the data can be acquired in real-time. In various embodiments, the data can be acquired periodically according pre-set time intervals.

As shown in FIG. 1, there are five receptacles 138 that are operatively coupled to the four pumping units. The unequal numbers between the receptacles and the pumping units are illustrated in FIG. 1 to highlight that the instrument system 100 may not include equal numbers of components and that a one-to-one match between individual components, such as between the receptacle 138a and the pumping unit "a" that includes the pump 120a, the nest 130a, the chip 132a and the needle 136a, may not be needed in certain hardware systems. The reason for having fewer number of pumping units may include for example, but not limited to, instrument footprint considerations or cost cutting measures associated with having fewer units that perform the same or substantially similar function. If the instrument system 100 can be coupled with an instrument workflow program that is designed to optimize the various operations within the workflow, it may be possible to compensate for having an unequal number of pumping units. The essence of having a fewer number of pumping units, for example as illustrated in FIG. 1, and yet the system that can be configured to work sufficiently enough to accommodate more receptacles is further described below.

The instrument system 100 also includes a plurality of chambers 140a and 140b (collectively referred to as "chambers 140"), a plurality of well plates 142a and 142b (collectively referred to as "well plates 142"), and a plurality of tubes 146. In various implementations, each of the chambers 140a and 140b can include an incubator. In various implementations, each of the chambers 140a and 140b can include a dedicated sample chamber sensor configured to acquire data from the respective sample chamber. In various implementations, the sensor can include a sensor for monitoring, for example, the temperature, humidity, etc. to provide environmental condition within the sample chamber. In various embodiments, the data can be acquired in real-time. In various embodiments, the data can be acquired periodically according pre-set time intervals.

FIG. 1 also shows that the instrument system 100 includes a stage 150 that can be configured to move in a uniaxial direction, bi-direction or tri-direction. In various implementations, the stage 150 can be configured to rotate on its axis to provide rotational movements in addition to one, two or three axes.

As shown in FIG. 1, the instrument system 100 also includes a laser 180, a projector 182, a camera 184 with its various objective lenses 186, and a plurality of filters 188. In various implementations, the laser 180 has a wavelength in the visible, UV, infrared, or any wavelength suitable for operating in the instrument system 100. In various implementations, the projector 182 can be a laser projector, a DSP projector, etc. In various implementations, the camera 184 can be a digital or a film camera, or any suitable image capture system. In various implementations, the objective lenses 186 include any suitable magnifications, including but not limited to 4×, 10×, 20×, 25×, 100×, etc. In various implementations, the plurality of filters 188 include any suitable color filters, including but not limited to, OEP, FITC, CYS, DAPI. These can collectively be considered to be instrument resources.

As described and shown in FIG. 1, in various implementations, the instrument system 100 includes a plurality of instrument resources, such as the pumps 120, the nests 130, the needles 136, the receptacles 138, the stage 150, the laser 180, the projector 182, the camera 184, the objectives 186, and the filters 188. In various implementations, the instrument system 100 includes a plurality of sample chambers 140, which include respective incubators, well plates 142, and the tubes 146.

As shown in FIG. 1, the instrument system 100 includes various physical components that are operationally coupled to other components in the instrument system 100. In instances of a component failure, for example, an instrument resource failure, where the instrument resource has multiple instances, e.g. the nest 130, can be alleviated during operation. For example, if the nest 130c fails, the other nests 130, namely nest 130a, nest 130b or nest 130d can be utilized in place of the failed nest 130c. Likewise, a failed pump or needle can be replaced by another pump or needle of the pumps 120 and the needles 136 should the need arises. In other words, the redundancy built into the instrument system 100 that has multiple modules or units can allow an instance of a failure of a single component to be readily alleviated or remedied. If a consumable material shown in FIG. 1, for example, the chips 132 or the fluid or reagent in the receptacles 138 is exhausted during operation, the instrument system 100 has a built-in redundancy to automatically change the instrument workflow program running on the instrument system 100 to preserve, for example, cells being cultured in the sample chambers 140 of the instrument system 100. In various embodiments, the instrument workflow program is a series of instrument operations that are to be executed by the instrument system 100 in accordance with a set order or timing interval.

Figure 2:
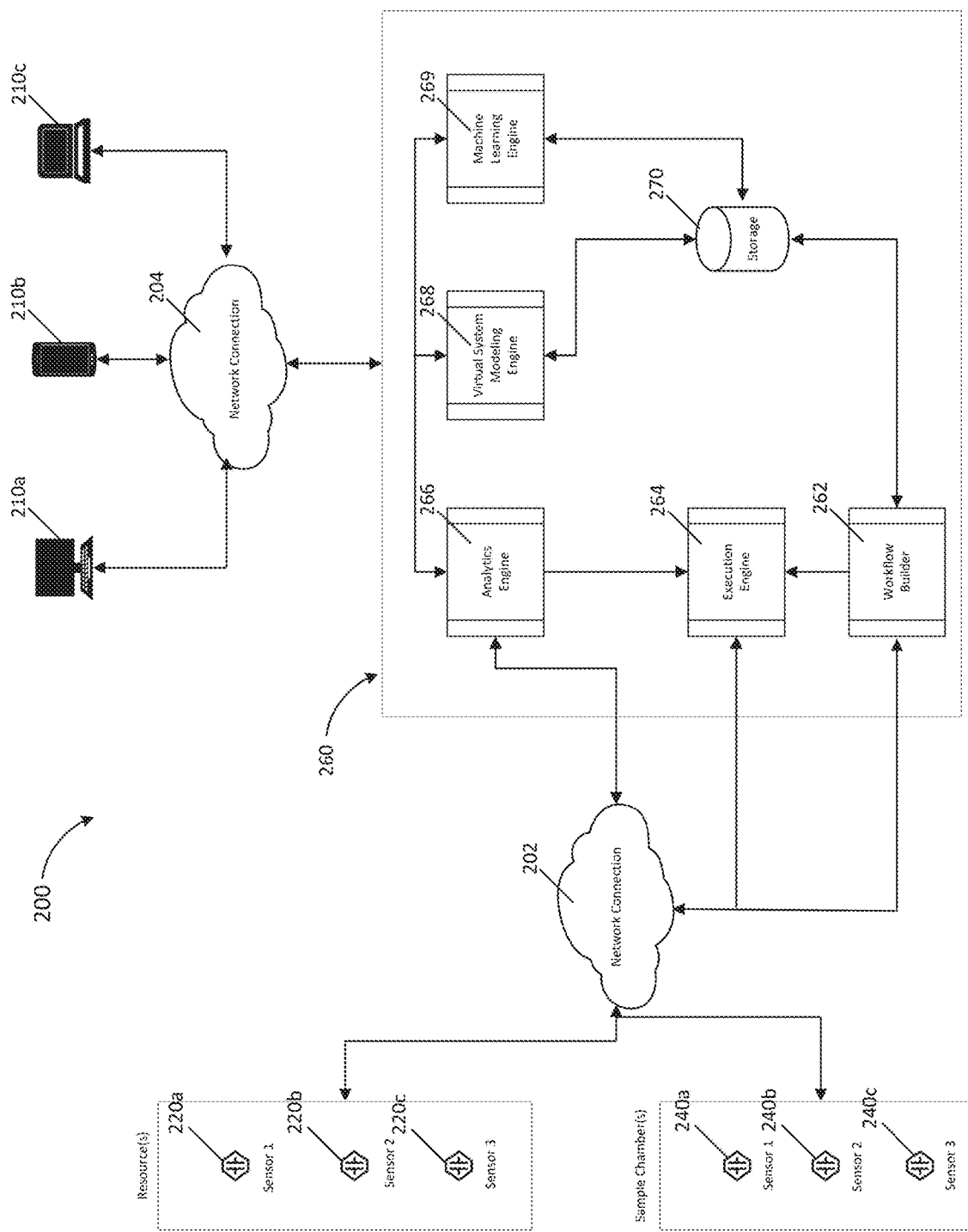
FIG. 2 shows an example system for dynamically optimizing an instrument workflow, according to various embodiments.

FIG. 2 shows an example system 200 for dynamically optimizing an instrument system workflow program, according to an illustrative implementation. As shown in FIG. 2, the system 200 includes a plurality of instrument resource sensors 220a, 220b, and 220c (collectively referred to as "resource sensors 220"), a plurality of sample chamber sensors 240a, 240b, and 240c (collectively referred to as "chamber sensors 240"), a computing device 260, and a plurality of external devices 210a, 210b, and 210c (collectively referred to as "external devices 210"). The computing device 260 further includes a software application or program comprising a workflow builder 262, an execution engine 264, an analytics engine 266, a virtual system modeling engine 268, and an optional machine learning engine 269, and a storage 270.

In various implementations, the resource sensors 220 are configured to monitor instrument resources that are similar or substantially similar to the plurality of instrument resources of the instrument system 100 described above and illustrated with respect to FIG. 1, such as the pumps 120, the nests 130, the needles 136, the receptacles 138, the stage 150, the laser 180, the projector 182, the camera 184, the objectives 186, and the filters 188. In various implementations, the chamber sensors 240 are configured to monitor the chambers that are similar or substantially similar to the plurality of sample chambers 140 of the instrument system 100 described above and illustrated with respect to FIG. 1. In various embodiments, the data can be acquired in real-time. In various embodiments, the data can be acquired periodically according pre-set time intervals.

In various implementations, the computing device 260 includes a personal computer, a portable computer, a main frame computer, a server, or a network server, etc. In various implementations, the workflow builder 262, the execution engine 264, the analytics engine 266, the virtual system modeling engine 268, or the optional machine learning engine 269 can be created within the software application or program that resides on the computing device 260. In various implementations, the software application or program can be a stand-alone application or a network application. A stand-alone application can reside on any of the aforementioned computing devices. A network application is any application that is stored on an application server (network server) connected to a network (e.g., local area network, wide area network, etc.) in accordance with any contemporary client/server architecture model and can be accessed via the network.

Figure 9:
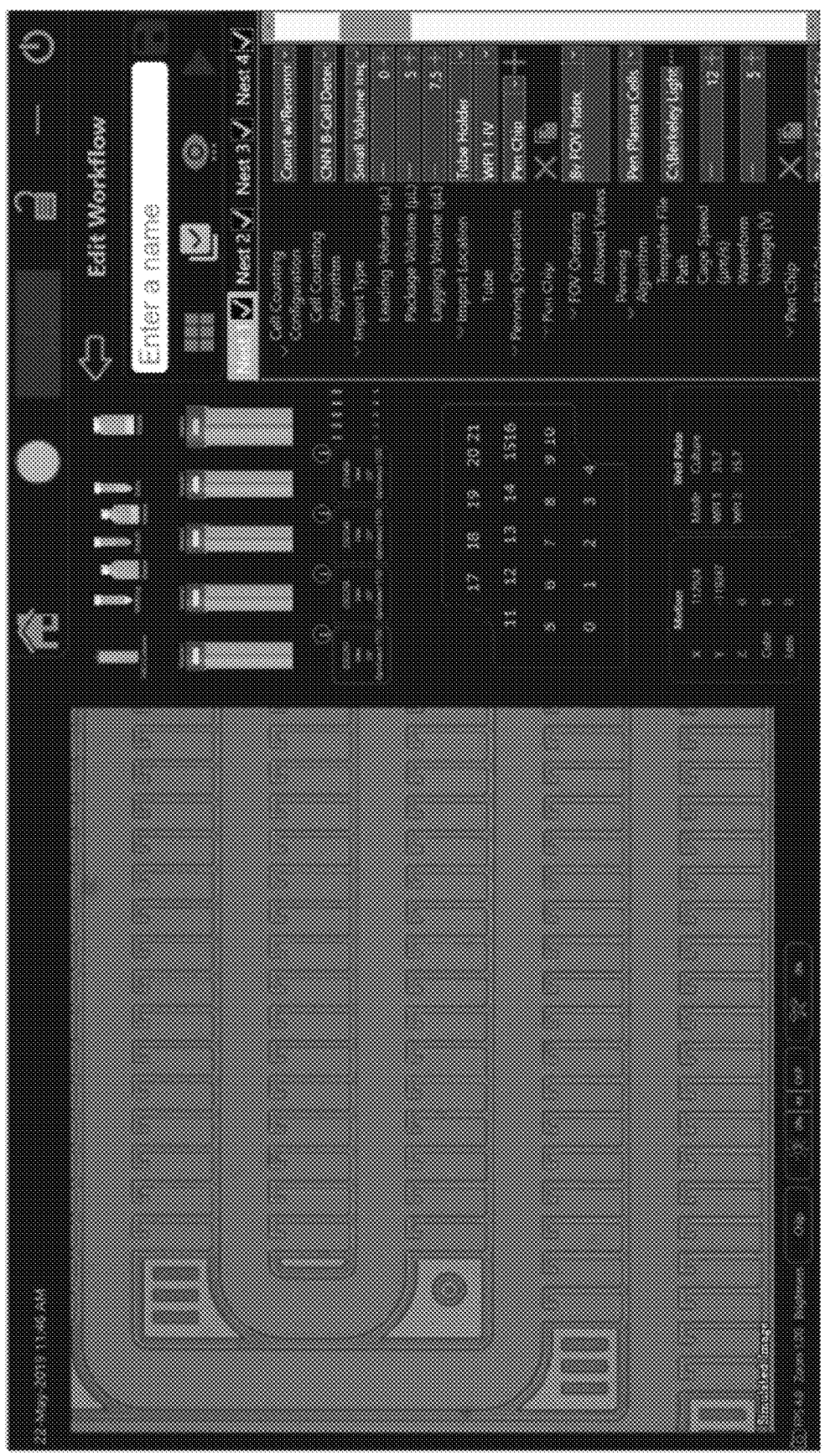
FIG. 9 is an illustration of a graphical user interface (GUI) that can be used by a system operator to build an instrument workflow, according to various embodiments.

In various implementations, the workflow builder 262 is configured to allow a user to create an instrument workflow program for the instrument system, such as the instrument system 100 shown and described in FIG. 1. In various embodiments, the instrument workflow program is a series of instrument operations that are to be executed by the instrument system 200 in accordance with a set order or timing interval. FIG. 9 illustrates, in accordance with various embodiments, an example graphic user interface (GUI) for allowing the user to populate the workflow builder with the parameters and operations necessary for user to conduct the desired instrument workflow program.

In various implementations, the execution engine 264 is configured to process the optimized instrument workflow program for the instrument system, such as the instrument system 100. In various implementations, the execution engine 264 acts as a device controller for executing instrument operations (as delineated by the instrument workflow program) by providing operating instructions to the one or more instrument resources and chambers.

In various implementations, the analytics engine 266 is configured to monitor data output from dedicated instrument resource sensors 220 and the dedicated chamber sensors 240. In various implementations, the analytics engine 266 is communicatively connected to the dedicated instrument resource sensors 220 and the dedicated chamber sensors 240. In various implementations, the analytics engine 266 is configured to initiate a calibration operation to update the virtual system model when a variance condition is detected in the real-time data output from the sensors 220 and/or 240. Examples of a variance condition can include, but are not limited to: low or empty reagent levels, reduced or total loss of function in the operation of the sample chamber, malfunction of an instrument system component, etc.

In various implementations, the virtual system modeling engine 268 is configured to optimize the instrument workflow program utilizing a virtual system model of the instrument system and generate an optimized instrument workflow program. In various implementations, the virtual system model is updated periodically, in real-time, or triggered by a variance condition or a user input. In various implementations, the virtual system model is updated at a set time interval or intervals, spanning from about 1 ms to about 24 hours, about 10 ms to about 12 hr, about 100 ms to about 1 hr, about 1 s to about 30 minutes, inclusive of any set time interval ranges therebetween.

In various implementations, the optional machine learning engine 269 can be configured to train the analytics engine 266 to improve the updated instrument workflow program. In various implementations, the optional machine learning engine 269 can be based on a generative adversarial network (GAN) to recognize the patterns of the workflow program and further improve the optimized or updated instrument workflow program.

In various implementations, the resources 220 and the chambers 240 are communicatively coupled to the computing device 260 via a wired or a wireless network, including for example, but not limited to telephone modem connections, wide area networks (WAN), local area networks (LAN), infrared data connections, bluetooth, NFC connections, TCP/IP, etc.

In various implementations, the resources 220 and the chambers 240 are housed in a housing that can be referred as a stand-alone instrument system. In various implementations, the stand-alone instrument system is similar to the instrument system 100 as described in FIG. 1. In various implementations, the stand-alone instrument system can be communicatively coupled to the computing device 260 via a wired or a wireless network connection 202, including for example, but not limited to telephone modem connections, wide area networks (WAN), local area networks (LAN), infrared data connections, Bluetooth, NFC connections, TCP/IP, etc.

In various implementations, the resources 220, the chambers 240 and the computing device 260 are housed in a housing that can be referred to as an integrated instrument system. In the integrated instrument system, the resources 220 and the chambers 240 are communicatively coupled to the computing device 260 via a wired connection. In various implementations, the connection can also be a wireless connection based on, for example, but not limited to telephone modem connections, wide area networks (WAN), local area networks (LAN), infrared data connections, bluetooth, NFC connections, TCP/IP, etc. In various implementations, any of the external devices 210a, 210b, or 210c can be communicatively coupled to the computing device 260 via a network 204.

In various implementations, any of the external devices 210a, 210b, or 210c can be communicatively coupled to the computing device 260 via a network connection 204, which can include telephone modem connections, wide area networks (WAN), local area networks (LAN), infrared data connections, Bluetooth, NFC connections, TCP/IP, etc.

Figure 3:
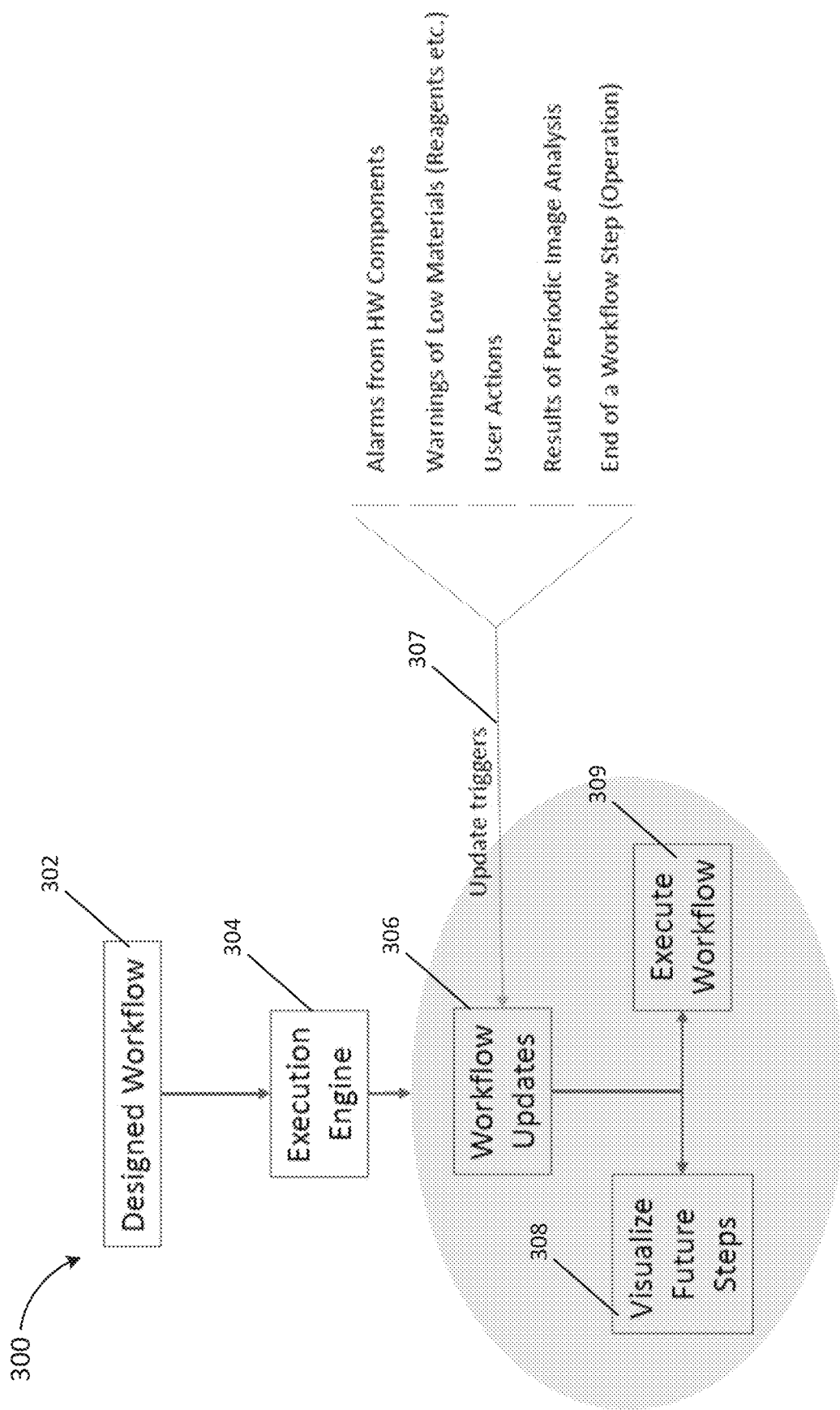
FIG. 3 illustrates an implementation of an instrument workflow program, according to various embodiments.

FIG. 3 illustrates an implementation of an instrument workflow program 300, according to an illustrative implementation. As illustrated in FIG. 3, the workflow program 300 includes stages of the workflow program, including a designed workflow 302, an execution engine 304, workflow updates 306, update triggers 307, visualize future steps 308 and execute workflow 309. Once the instrument workflow program is designed and created at 302, the execution engine 304 takes over and execute the operations included in the workflow program. Based on the current conditions of the instrument system, it creates a plan for the workflow and starts executing the workflow program. The execution is based on the current state of the instrument maintained in the instrument model. As shown in FIG. 3, the workflow is being updated periodically or triggered by one of the update triggers 307, which is also referred to herein as "variance condition". In various implementations, the user can interact with the timeline during the execution of the workflow program. Interactions can include a visual means of interacting with the workflow program. In some instances, the user may not directly update the workflow program, but may stop individual operations within the workflow program. As shown in FIG. 3, the update triggers 307 can include for example, but not limited to an alarm from a hardware component, such as from a sensor of an instrument resource or a sample chamber, a warning of low material detected by a sensor from an instrument resource, such as a receptacle, a user action, a result of a periodic image analysis or an end of workflow step notification. When one of the update triggers 307 occurs, the workflow program is updated. As shown in FIG. 3, based on the updated workflow program, a set of future operational steps can be visualized and executed.

Figure 4:
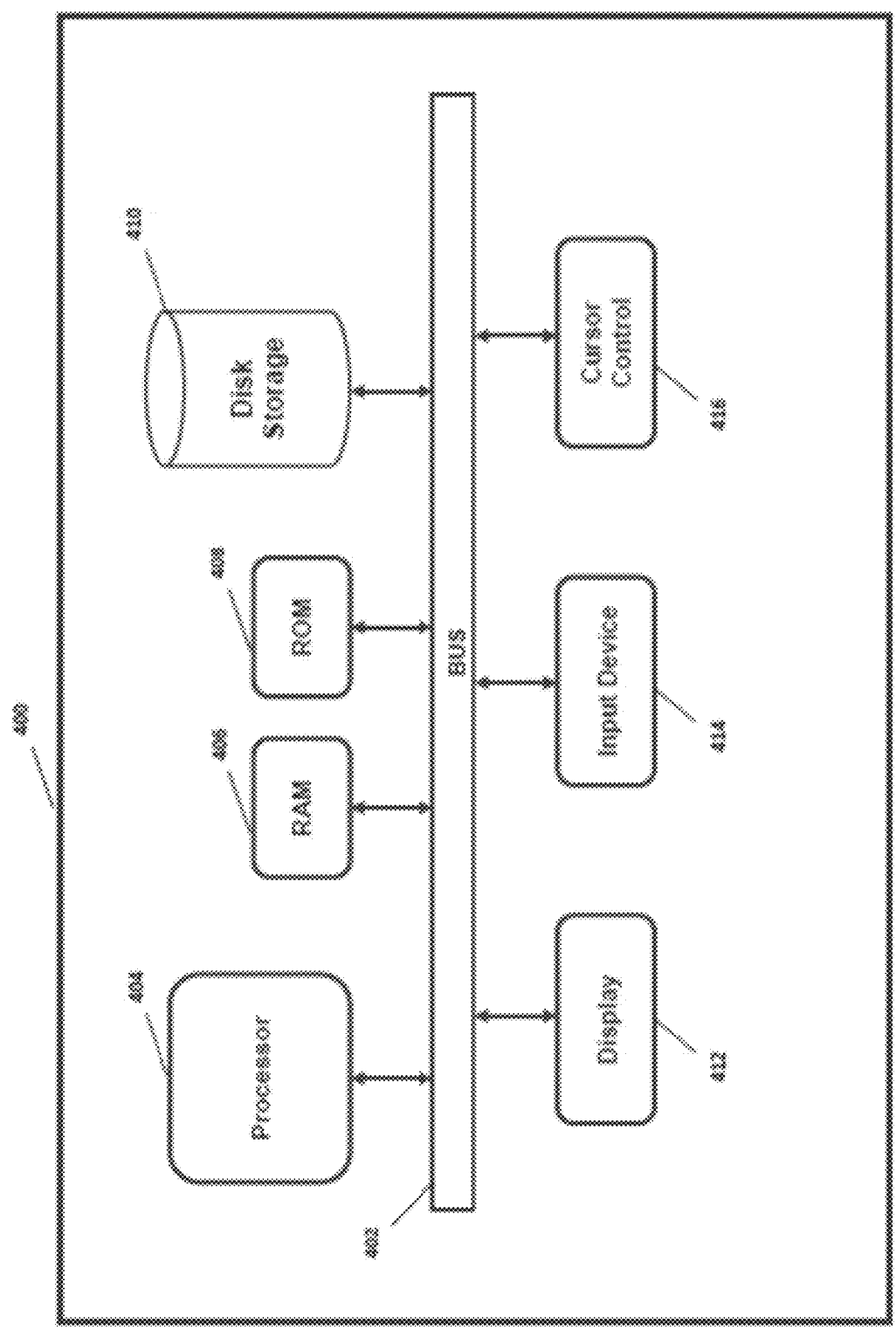
FIG. 4 is a block diagram that illustrates a computer system, according to various embodiments.

FIG. 4 is a block diagram that illustrates a computer system 400, upon which embodiments of the present teachings may be implemented. In various embodiments of the present teachings, computer system 400 can include a bus 402, or other communication mechanism for communicating information, and a processor 404 coupled with bus 402 for processing information. In various embodiments, computer system 400 can also include a memory, which can be a random-access memory (RAM) 406, or other dynamic storage device, coupled to bus 402 for determining instructions to be executed by processor 404. Memory also can be used for storing temporary variables or other intermediate information during execution of instructions to be executed by processor 404. In various embodiments, computer system 400 can further include a read only memory (ROM) 408 or other static storage device coupled to bus 402 for storing static information and instructions for processor 404. A storage device 410, such as a magnetic disk or optical disk, can be provided and coupled to bus 402 for storing information and instructions.

In various embodiments, computer system 400 can be coupled via bus 402 to a display 412, such as, for example, a cathode ray tube (CRT), a liquid crystal display (LCD) or a light emitting diode (LED) display, for displaying information to a computer user. An input device 414, including alphanumeric and other keys, can be coupled to bus 402 for communicating information and command selections to processor 404. Another type of user input device is a cursor control 416, such as a mouse, a trackball or cursor direction keys for communicating direction information and command selections to processor 404 and for controlling cursor movement on display 412. This input device 414 typically has two degrees of freedom in two axes, a first axis (i.e., x) and a second axis (i.e., y), that allows the device to specify positions in a plane. However, it should be understood that input devices 414 allowing for 3 dimensional (x, y and z) cursor movement are also contemplated herein.

Consistent with certain implementations of the present teachings, results can be provided by computer system 400 in response to processor 404 executing one or more sequences of one or more instructions contained in memory 406. Such instructions can be read into memory 406 from another computer-readable medium or computer-readable storage medium, such as storage device 410. Execution of the sequences of instructions contained in memory 406 can cause processor 404 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 404 for execution. Such a medium can take many forms, including but not limited to, non-volatile media, volatile media, and transmission media. Examples of non-volatile media can include, but are not limited to, optical, solid state, magnetic disks, such as storage device 410. Examples of volatile media can include, but are not limited to, dynamic memory, such as memory 406. Examples of transmission media can include, but are not limited to, coaxial cables, copper wire, and fiber optics, including the wires that comprise bus 402.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 404 of computer system 400 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein flow charts, diagrams and accompanying disclosure can be implemented using computer system 400 as a stand-alone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 400 of FIG. 4, whereby processor 404 would execute the analyses and determinations provided by these engines, subject to instructions provided by any one of, or a combination of, memory components 406/4008/410 and user input provided via input device 414.

Figure 5:
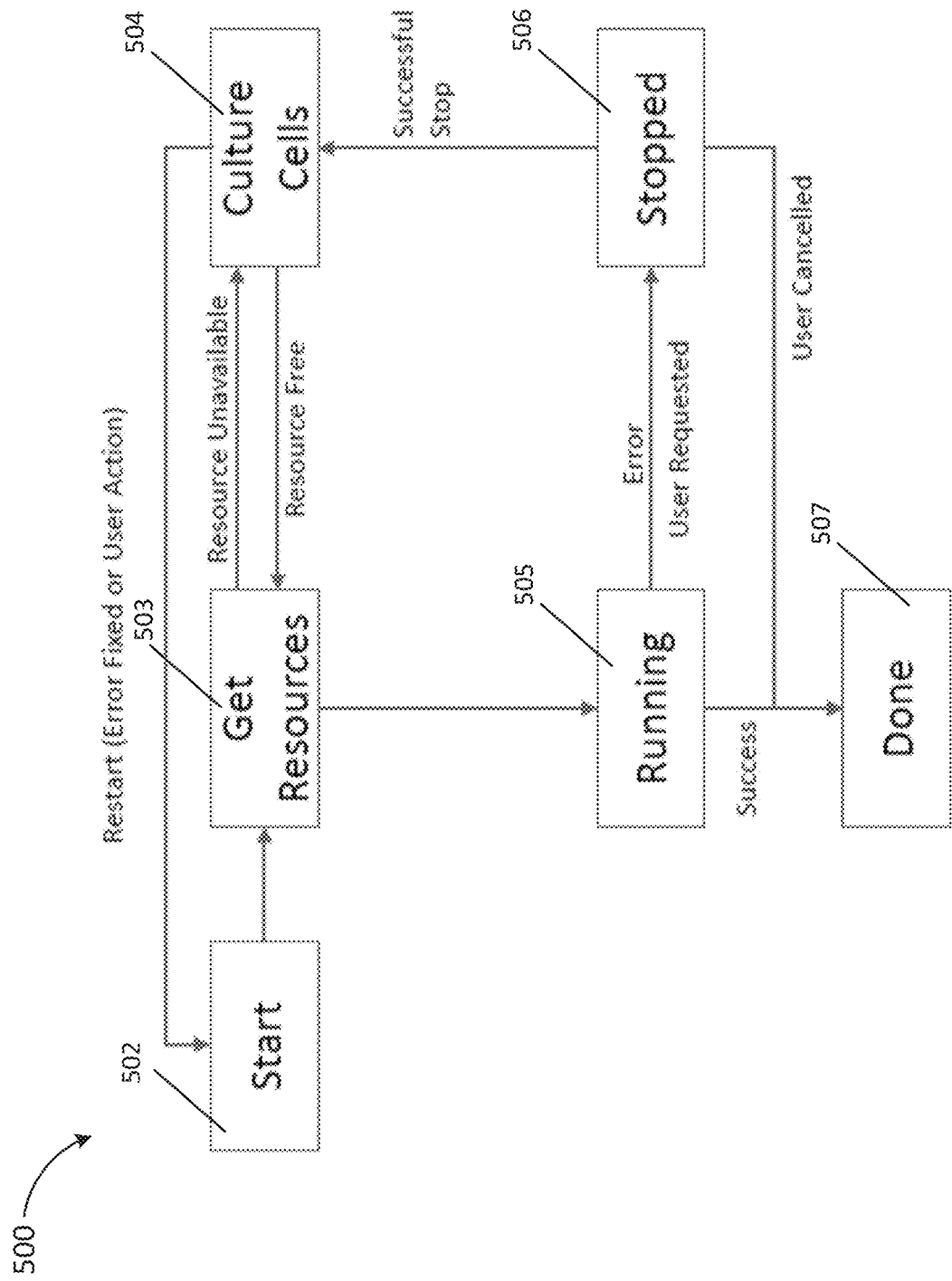
FIG. 5 illustrates an implementation of an instrument workflow program operation, according to various embodiments.

FIG. 5 illustrates an implementation of an instrument workflow program operation 500, according to an illustrative implementation. The operation 500 includes various stages of the workflow program operation, including start 502, get resources 503, culture cells 504, running 505, stopped 506 and done 507. After starting the operation at 502, the operation obtain resources at 503. If resources are available, the operation begins running at 505 for culture cells at 504. The operation stops at 506 when an error occurred or upon a user request. If resources are unavailable, the operation can restart when the resources are available.

Figure 6:
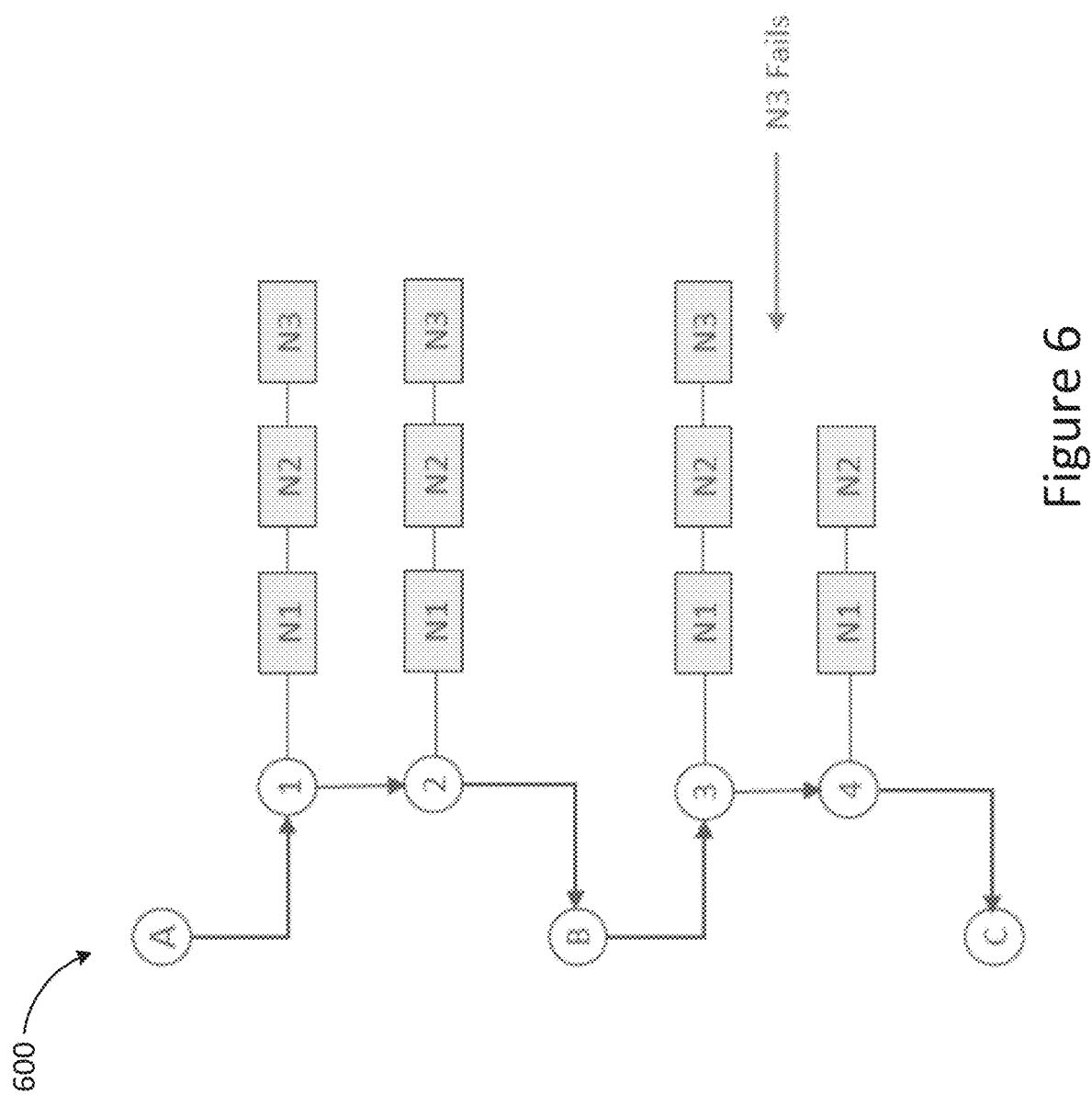
FIG. 6 illustrates an implementation of an instrument workflow hierarchy, according to various embodiments.

FIG. 6 illustrates an implementation of an instrument workflow hierarchy 600, according to an illustrative implementation. The hierarchy 600 includes parent operations A, B, and C, and leaf operations 1, 2, 3, and 4. Parent operations A, B, and C perform management tasks, while leaf operations 1, 2, 4, and 4 execute actions on instrument resources, such as nest N1, nest N2 and nest N3. For example, when the instrument workflow begins from parent operation A, the leaf operation 1 is performed on nest N1, nest N2 and nest N3. The workflow continues at leaf operation 2, then at parent operation B, then leaf operation 3. After leaf operation 3, the nest N3 fails and the workflow program continues to leaf operation 4, which is performed on nest N1 and nest N2. The dynamic scheduling is possible since each parent operation can respond to available resources when it starts when nest N3 fails.

Figure 7:
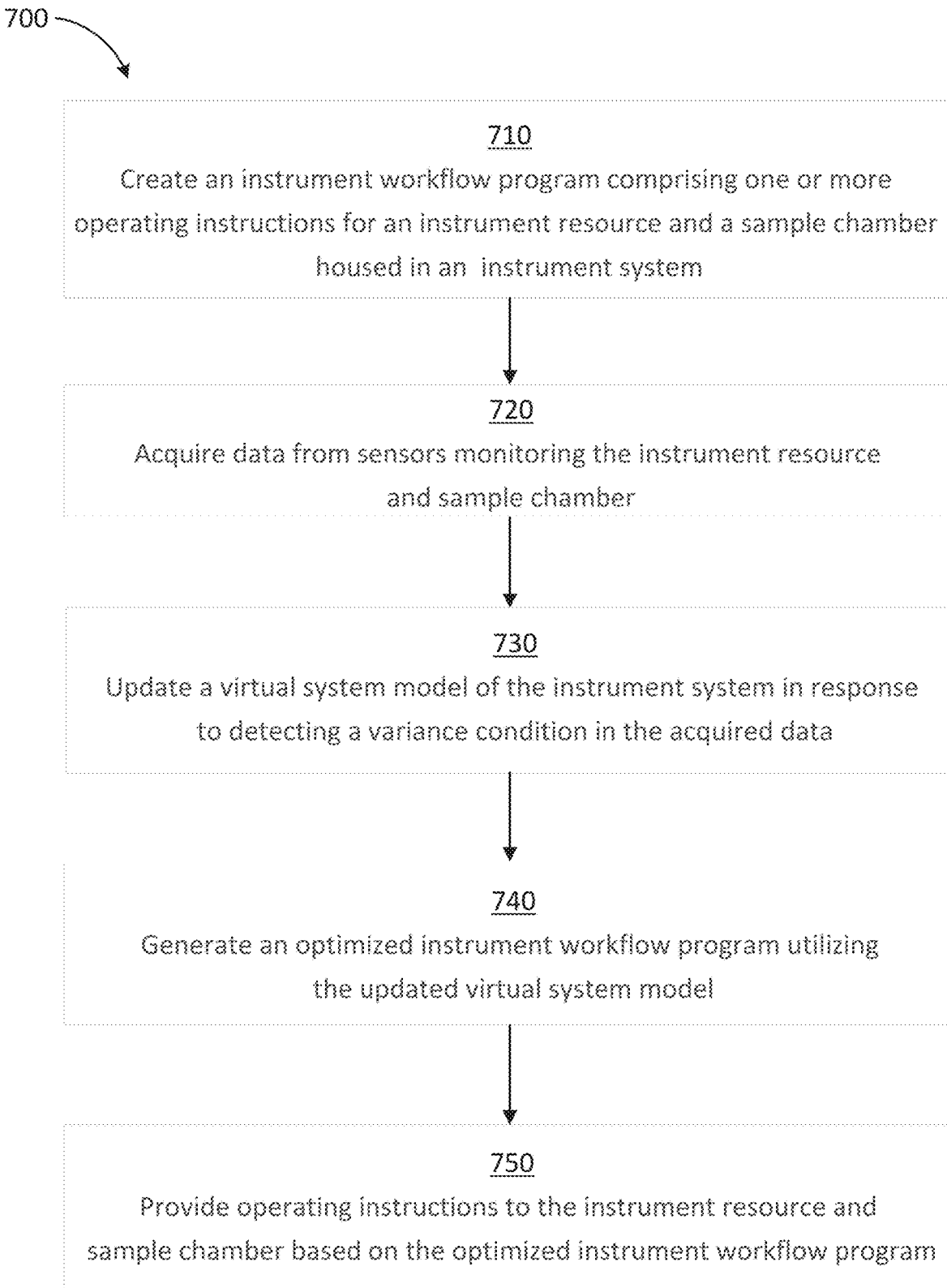
FIG. 7 is a flowchart of an example method for dynamically optimizing an instrument system workflow, according to various embodiments.

FIG. 7 is a flowchart of an example method 700 for dynamically optimizing an instrument system workflow, according to an illustrative implementation. The method 700 includes creating an instrument workflow program comprising one or more operating instructions for an instrument resource and a sample chamber housed in an instrument system at step 710. The method 700 also includes acquiring data from sensors monitoring the instrument resource and sample chamber at step 720. In various embodiments, the data can be acquired in real-time. In various embodiments, the data can be acquired periodically according pre-set time intervals.

The method 700 also includes updating a virtual system model of the instrument system in response to detecting a variance condition in the acquired data at step 730. Examples of a variance condition can include, but are not limited to: low or empty reagent levels, reduced or total loss of function in the operation of the sample chamber, malfunction of an instrument system component, etc.

The method 700 further includes generating an optimized instrument workflow program utilizing the updated virtual system model at step 740. The method 700 also includes providing operating instructions to the instrument resource and sample chamber based on the optimized instrument workflow program at step 750. An optimized instrument workflow program is one that results in the utilization of instrument resources in as efficient (in resource time or resources) a manner as possible to service the one or more sample chambers.

Figure 8:
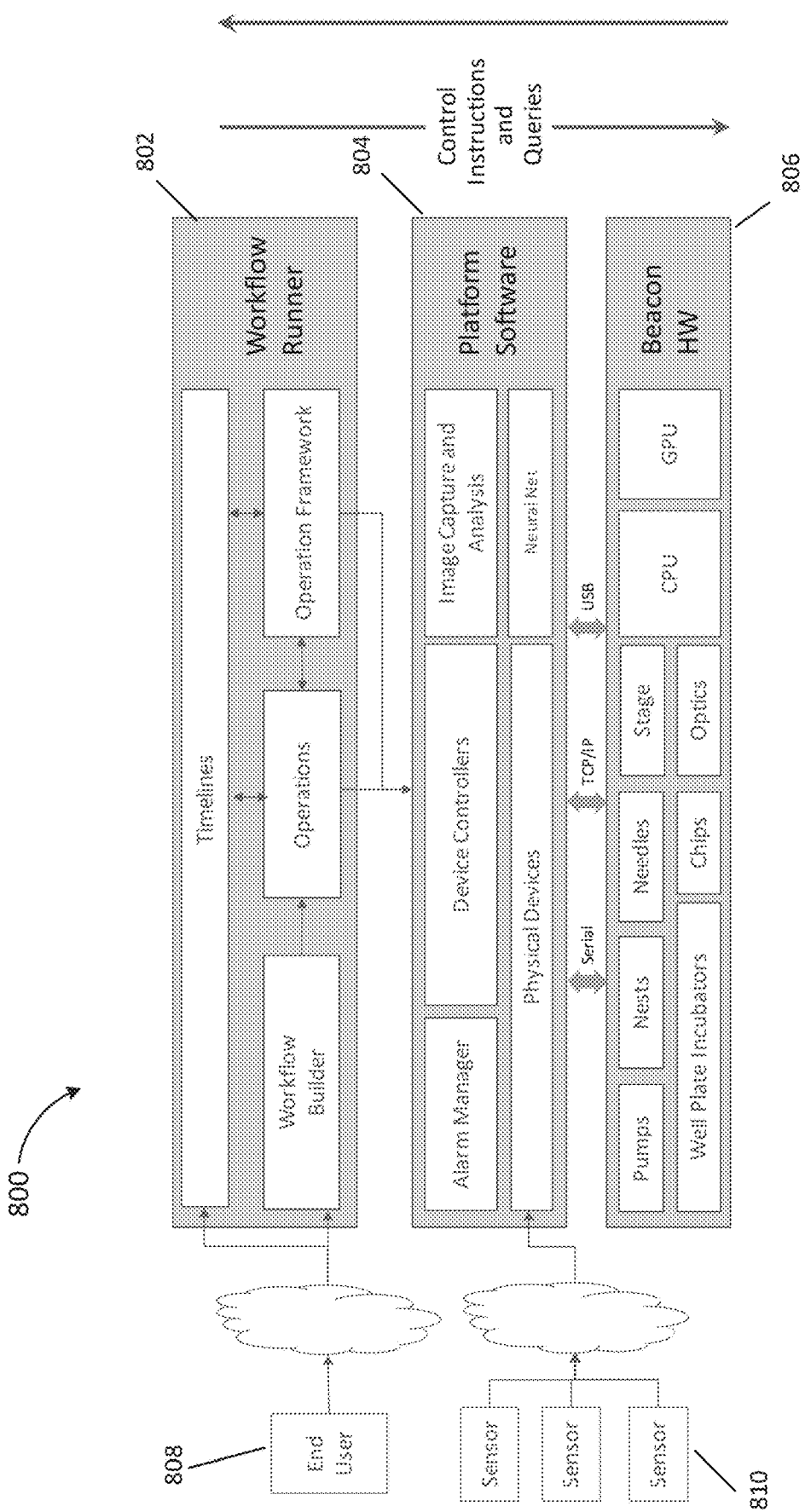
FIG. 8 is a diagram detailing the operation of an example system for dynamically optimizing an instrument workflow, according to various embodiments.

FIG. 8 is a diagram detailing the operation of an example system for dynamically optimizing an instrument workflow, according to various embodiments.

As depicted herein, the system 800 includes an instrument hardware layer (e.g., BEACON™) 806, instrument platform software layer 804 and an instrument workflow framework layer 802. It should be noted that the functionality of software layer 804 and framework layer 802 is hardware layer agnostic. As such, while FIG. 8 illustrates "Beacon HW" as the instrument hardware layer, this is simply an instrument hardware layer example and any other instrument hardware layers can be contemplated that could apply the functionality of software layer 804 and framework layer 802.

The instrument workflow framework layer 802 is configured to allow a user 808 to create an instrument workflow program to be performed by the instrument hardware layer 806. The instrument workflow program is a series of operations that can be executed by an operations framework that calls on one or more device controllers (resident on the instrument platform software layer 804) to instruct one or more instrument resources (resident in the instrument hardware layer 806) to perform a predetermined task. The timing of each of the series of operations may be adjusted (to optimize the time to complete the instrument workflow program) based on feedback received from at least one instrument resource/sample chamber sensor 810 (communicatively connected to the instrument platform software layer 804) and/or any additional input received from an end user 808. Further, the system 800 can include a workflow modeling component (resident in the instrument platform software layer 804) configured to receive data from the operations framework and, optionally, the operations in the series of operations to maintain a model of the status of the instrument workflow program based upon the received data.

In various embodiments, a machine learning engine (resident in the instrument platform software layer 804) can be configured to work with the operations framework to improve the timing of the calling of operations and thereby further optimize the time to completion of the workflow program. In various embodiments, the operations framework adjusts the calling of operations in real-time. In various embodiments, that instrument resources, can include, but are not limited to: pumps, input/output needles, an incubator, a holder for a sample chamber, a stage, optical train, etc.

In various embodiments, the system can include an incubator that is configured to hold a well plate. In various embodiments, each instrument resource can include an instrument resource sensor configured to acquire data form the instrument resource.

In various embodiments, the sample chamber holder is a nest and the sample chamber is a microfluidic device. In various embodiments, the system is comprised of a plurality of sample chamber holders.

In various embodiments, the sample chamber sensor comprises an optical train that includes a camera configured to image the sample chamber. In various embodiments, the optical train is further comprised of a projector and/or a laser.

In various embodiments, the system 800 is comprised of a plurality of receptacles.

In various embodiments, the system 800 is further comprised one or more holders for sample containers used to hold pre- or post-processed sample. In various embodiments, the sample container holders are configured to hold a tube or a well plate.

In various embodiments, the data received by the operations framework from the instrument resource sensor is received directly from the instrument resource sensor.

In various embodiments, the data received by the operations framework from the at least one instrument resource sensor is received indirectly from an operation that instructed the corresponding instrument resource.

In various embodiments, the additional user input received by the operations framework is received indirectly from the workflow modeling component.

In various embodiments, the set of operations comprises operations for loading a sample into the sample chamber, detecting micro-objects located within the sample chamber, relocating micro-objects detected in the sample chamber, supplying one or more reagents to the sample chamber, assaying micro-objects detected in the sample chamber, and exporting micro-objects from the sample chamber.

In various embodiments, the workflow modeling component maintains a real time model of the status of the workflow program based upon the received data.

In various embodiments, the model of the status of the workflow program maintained by the workflow modeling component is displayed on a graphical user interface, wherein the workflow modeling component is further configured to instruct the user to perform specific tasks during the performance of the workflow program.

In various embodiments, the workflow modeling component is further configured to request additional user input during the performance of the workflow program, wherein the additional user input is passed along to the operations framework.

In various embodiments, the data received by the operations framework comprises an alarm indicating that a one or more operations in the series of operations cannot be completed, a warning of low material detected in the one or more receptacles, a result from an analysis of an image of the sample chamber, or completion of an operation in the series of operations.

In various embodiments, the one or more instrument resources, the sample chamber holder, and the one or more receptacles are housed within a housing.

In various embodiments, the one or more instrument resources, the sample chamber holder, the one or more receptacles, and the computing device are housed within a housing.

FIG. 9 is an illustration of a graphical user interface (GUI) that can be used by a system operator to build an instrument workflow, according to various embodiments. As depicted herein, the workflow builder (depicted in the right panel) can allow a user to select the operation and customize the operation for the particular application.

Figure 10:
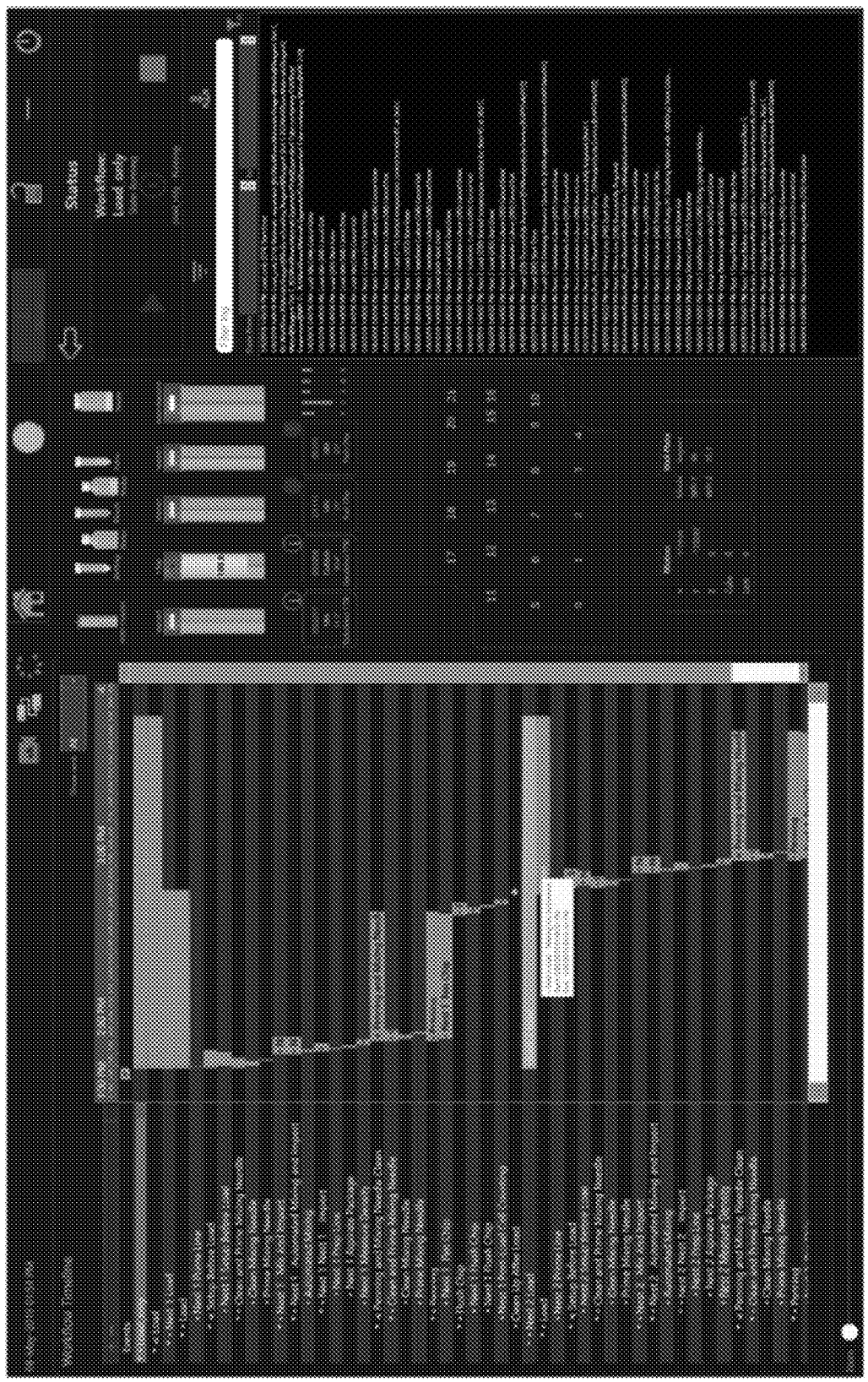
FIG. 10 is an illustration of a GUI that depicts the progress of an instrument workflow in operation, according to various embodiments.

FIG. 10 is an illustration of a GUI that depicts the progress of an instrument workflow in operation, according to various embodiments. As depicted herein, the GUI shows a workflow in progress and the left panel of the GUI shows the workflow steps and the timeline of the set of operations.

Figure 11:
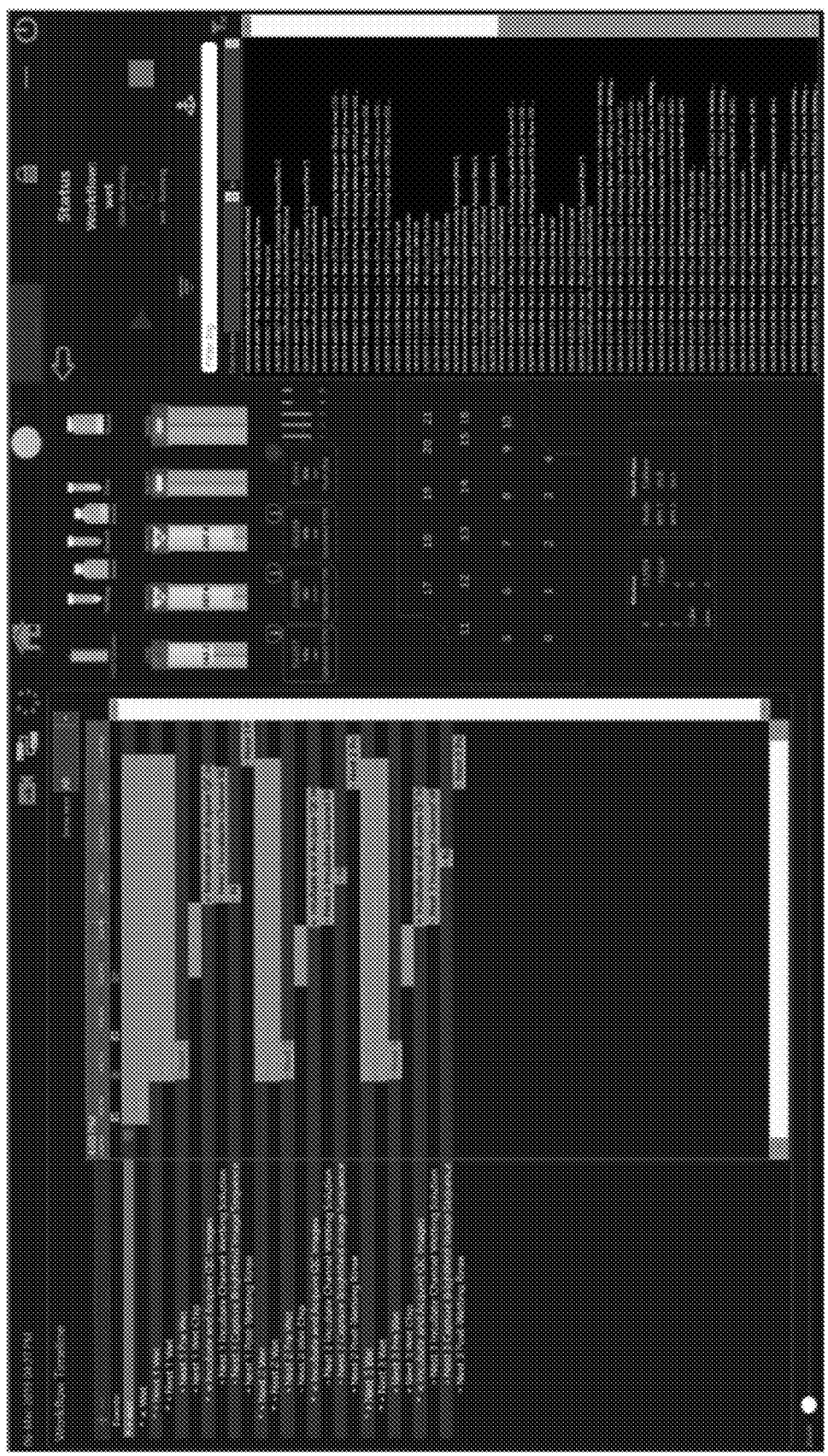
FIG. 11 is an illustration of a GUI that depicts the progress of an instrument workflow in operation, according to various embodiments.

FIG. 11 is an illustration of a GUI that depicts the progress of an instrument workflow in operation, according to various embodiments. As depicted herein, the GUI shows a shorter workflow and multiple nests active at the same time.

Figure 12:
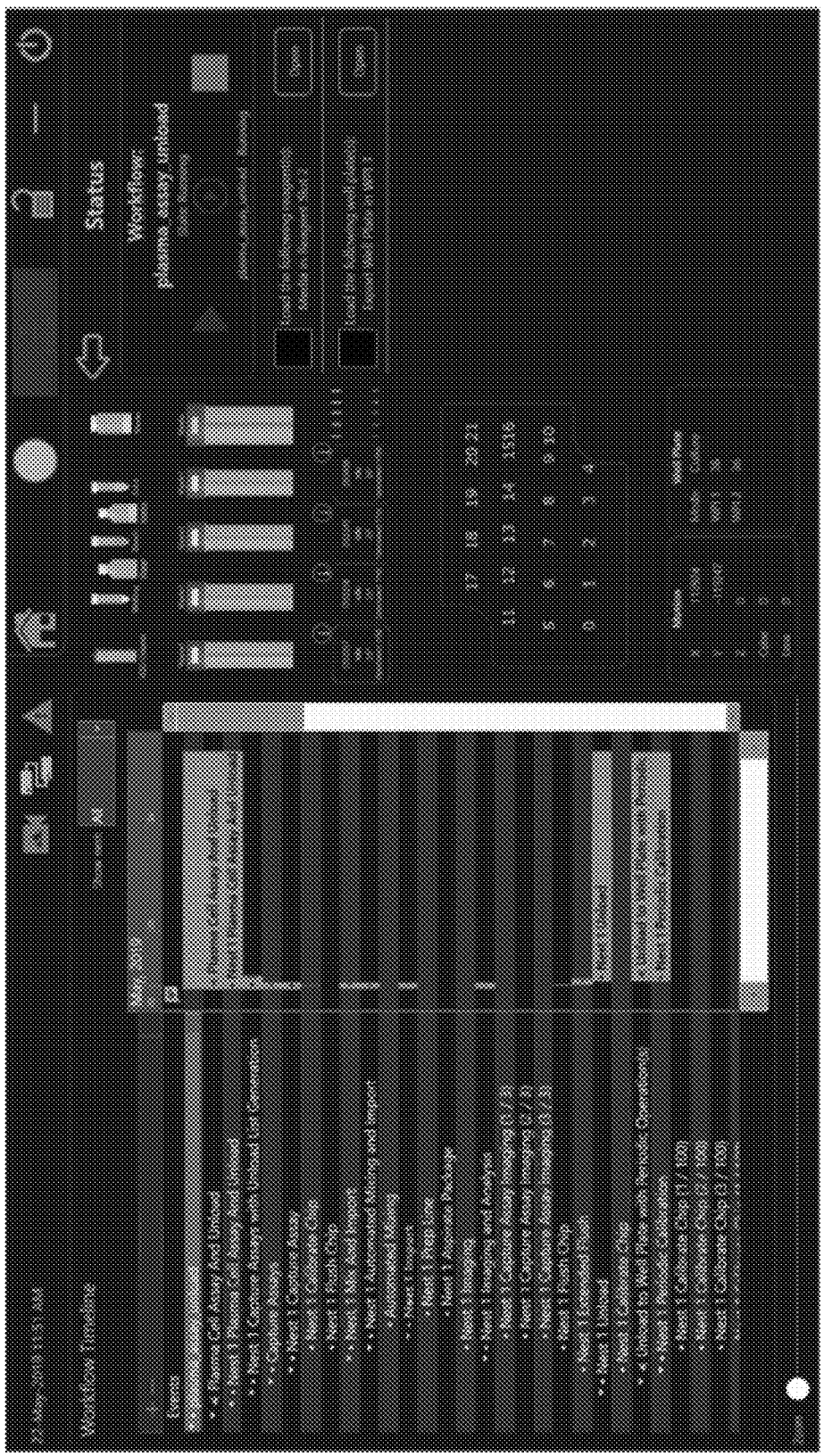
FIG. 12 is an illustration of a GUI that depicts the progress of an instrument workflow in operation, according to various embodiments.

FIG. 12 is an illustration of a GUI that depicts the progress of an instrument workflow in operation, according to various embodiments. As depicted herein, the GUI shows the user being prompted for further input and/or attention to an alert.

In relation to the virtual system model, and in accordance with various embodiments, generally after workflow builder 262, via a GUI (e.g., illustrated in FIG. 9), enables the creation of the user-desired instrument workflow program for the instrument platform, the GUI can then output the created full workflow for user viewing and necessary interaction. The illustrated workflow (e.g., in the form of a timeline as provided in FIG. 13A discussed below) can provide a visual mapping between a logical process (i.e., the workflow) and the components of the instrument platform that will execute the workflow. Since automation is a critical component of advanced instrument platform, one key feature is to provide users the knowledge of when they will be expected to interact with the overall system. This knowledge can be conveyed through stage gates called touchpoints. Touchpoints will be discussed in more detail below. It should be noted that to provide as efficient an automated and interactive system as possible, a software portion of the system can minimize the number of touchpoints. This can be done, for example by aggregating touchpoints to minimize user back and forth. Moreover, touchpoints can be brought forward where possible, particularly where the components of the instrument platform are in such a state to allow such aggregation and advancement. Again, this will be discussed in further detail below. To understand how touchpoints work, one should understand the features of the workflow and associated GUI that give rise to these touchpoints.

Figure 13A:
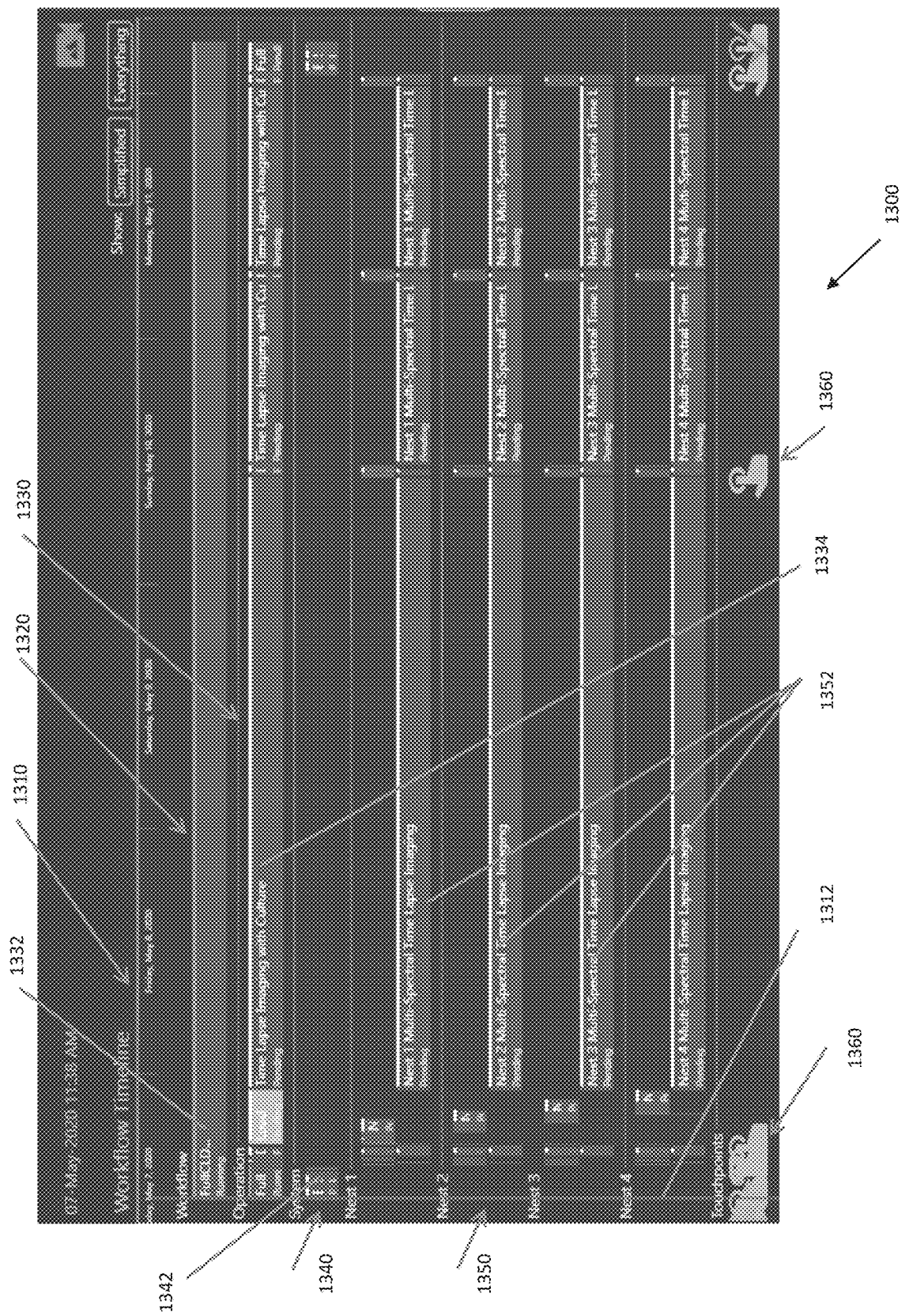
FIGS. 13A and 13B are illustrations of a GUI that depicts the progress of an instrument workflow in operation, according to various embodiments.
Figure 13B:
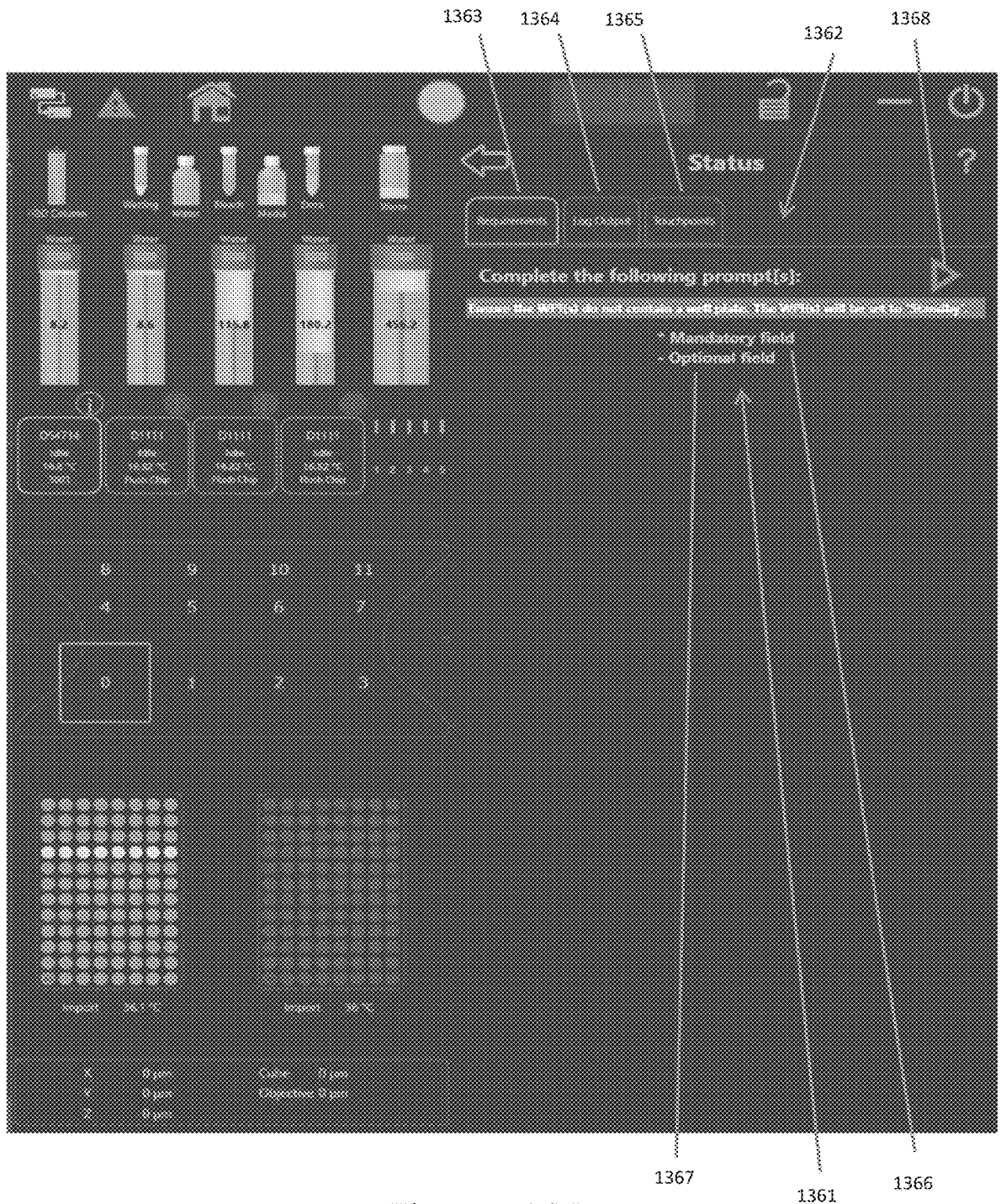

FIGS. 13A and B, for example, provides the two panels of a GUI 1300 that illustrates a full five-day workflow, in this case for cell line development. Though FIGS. 13A and 13B show two different example panels of a GUI, the example panels provided can be, and will be discussed below, as a single GUI 1300. In accordance with various embodiments, GUI 1300 can display various features necessary to communicate various key components of the user-defined workflow discussed above with reference to FIG. 9. For example, GUI 1300 can include a time window 1310. Time window 1310 can be divided into any contemplated timeframe. For example, the timeframe displayed can be anywhere from five minutes to the amount of time needed to complete the workflow (e.g., 8 hours, 12 hours, 16 hours, 20 hours, one day, two days, three days, four days, five days, one week, two weeks, or longer). The time window can be configurable. In FIG. 13A, that time window 1310 is divided by days and displays the entire five day protocol. A current time indicator 1312 can be provided as part of time window 1310, indicating the current time of day. Current time indicator 1312 can be provided in many forms. In FIG. 13A, indicator 1312 is represented by a vertical bar that intersects each of the associated operations displays (workflow, operation, system and nest, all discussed below) and touchpoints (also discussed below) associated with that specific time frame in the workflow.

In accordance with various embodiments, GUI 1300 can further include a workflow display 1320 for the entire workflow period (in this case, five days).

In accordance with various embodiments, GUI 1300 can also include an operations display 1330 that illustrates various operations set to occur, under normal working conditions across the time window. Operations display 1330 can display various operations, depending on the progress of the workflow, including completed operations (not pictured), in-process operations 1332, and future operations 1334. There are various ways to differentiate between completed, in-process and future operations. In FIG. 13A, these differences are illustrated by an associated color bar across the top of the operation. For example, completed operations can be represented by a blue bar, in-process operations by a green bar, and future operations by a white bar. Again, differentiation can take any form necessary to communicate completed from in-process and from future operations. FIG. 13A's representation is simply an example form of differentiation.

In accordance with various embodiments, GUI 1300 can also include a system display 1340 that also illustrates various system operations 1342 set to occur, under normal working conditions, across the time window. Operations 1342 of system display 1340 can differ from the operations illustrated in operations display 1330. In accordance with various embodiments, system operations 1342 can include operations that lock down the overall system until those associated tasks are performed. Operations 1342 can include, for example, a full clean step, diagnostics, etc. Similar to the operations display, system display 1340 can display various operations, depending on the progress of the workflow, including completed operations, in-process operations, and future operations. There are various ways to differentiate between completed, in-process and future operations. In FIG. 13A, these differences are illustrated by an associated color bar across the top of the operation. For example, completed operations can be represented by a blue bar, in-process operations by a green bar, and future operations by a white bar. Again, differentiation can take any form necessary to communicate completed from in-process and from future operations.

In accordance with various embodiments, GUI 1300 can also include one more nest operation displays 1350. The number of provided displays 1350 depends on the number of nests being utilized on the system. In FIG. 13A, there are four nest operations displays 1350. Similar to operations display 1330 and system display 1340, display 1350 can illustrate nest operations 1352 unique to one or more of the nest in use. Again, similar to the operations display, nest operations display 1350 can display various operations, depending on the progress of the workflow, including completed operations, in-process operations, and future operations. There are various ways to differentiate between completed, in-process and future operations. In FIG. 13A, these differences are illustrated by an associated color bar across the top of the operation. For example, completed operations can be represented by a blue bar, in-process operations by a green bar, and future operations by a white bar. Again, differentiation can take any form necessary to communicate completed from in-process and from future operations.

In accordance with various embodiments, GUI 1300 can also include one or more touchpoint images (or "touchpoints") 1360. The touchpoint image can take the form of a symbol, a graphic design, or the like. Touchpoints 1360 can be provided, as shown in FIG. 13, horizontally along the workflow timeline. As discussed above, since automation is a critical component of advanced instrument platform, one key feature is to provide users the knowledge of when they will be expected to interact with the overall system through, for example, touchpoints 1360. To provide as efficient an automated and interactive system as possible, a software portion of the system can minimize the number of touchpoints. This can be done, for example by aggregating touchpoints to minimize user back and forth. Moreover, touchpoints can be brought forward where possible, particularly where the components of the instrument platform are in such a state to allow such aggregation and advancement. By aggregating and/or moving forward the position of the touchpoints in the timeline, gaps between touchpoints can be maximized or otherwise adjusted to avoid touchpoints during undesirable times, such as during the night (e.g., between the hours of 6 pm and 8 am).

Referring to FIG. 13B, for each touchpoint 1360, one or more associated requirements 1361 can be provided in a status window 1362. The status window 1362 can include various tabs including, for example, a requirements tab 1363, a log output tab 1364, and a touchpoints tab 1365. The requirements 1361 can include fields for mandatory requirements 1366 and optional requirements 1367.

Regarding requirements 1361, any contemplated indicator can be used to differentiate mandatory requirements 1366 and optional requirements 1367. In FIG. 13B, for example, an "*" can be used to indicate a mandatory requirement and a "-" can be used to indicated an optional requirement. In FIG. 13B, the requirement listed states "Ensure the WPI(s) do not contain a well plate. The WPI(s) will be set to 'Standby'" (WPI being Well Plate Incubator). Status window 1362 also includes a button 1368 that a user can click once requirements are met. In FIG. 13B, button 1368 is in the form of a sideways triangle (i.e., "play" button), though any contemplated button design can be considered.

Figure 14A:
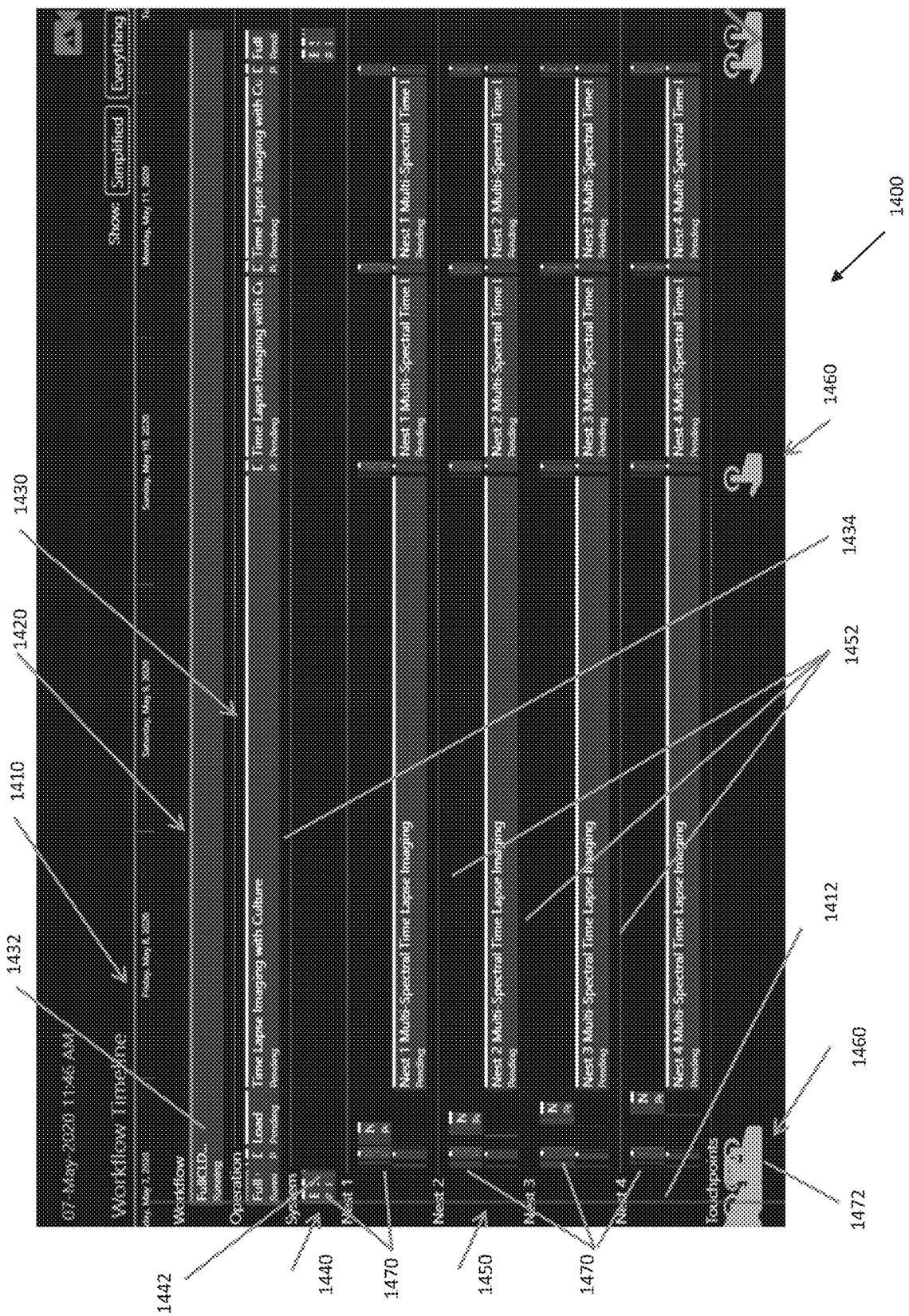

FIGS. 14A to 14G illustrate example GUI 1400, in accordance with various embodiments. Similar to GUI 1300 provided in FIGS. 13A and B, FIGS. 14A to 14G provide the two panels of a GUI 1400 that illustrates a full five-day workflow, in this case, for cell line development. Though FIGS. 14A and 14G show two different example GUI display panels, the example display panels provided can be, and will be discussed below, as a single GUI 1400.

In accordance with various embodiments, GUI 1400, similar to GUI 1300, can display various features necessary to communicate various key components of the user-defined workflow discussed above with reference to FIG. 9. For example, GUI 1400 can include a time window 1410. Time window 1410 can be divided into any contemplated timeframe. For example, the timeframe displayed can be anywhere from five minutes to five days. In FIG. 14A, that time window 1410 is divided by days and displaying the entire five day protocol. A current time indicator 1412 can be provided as part of time window 1410, indicating the current time of day. Current time indicator 1412 can be provided in many forms. In FIG. 14A, indicator 1412 is represented by a vertical bar that intersects each of the associated operations displays (workflow, operation, system and nest, all discussed below) and touchpoints (also discussed below) associated with that specific time frame in the workflow.

In accordance with various embodiments, GUI 1400 can further include a workflow display 1420 for the entire workflow period (in this case, five days).

In accordance with various embodiments, GUI 1400 can also include an operations display 1430 that illustrates various operations set to occur, under normal working conditions across the time window. Operations display 1430 can display various operations, depending on the progress of the workflow, including completed operations (not pictured), in-process operations 1432, and future operations 1434. There are various ways to differentiate between completed, in-process and future operations. In FIG. 14, these differences are illustrated by an associated color bar across the top of the operation. For example, completed operations can be represented by a blue bar, in-process operations by a green bar, and future operations by a white bar. Again, differentiation can take any form necessary to communicate completed from in-process and from future operations. FIG. 14's representation is simply an example form of differentiation.

In accordance with various embodiments, GUI 1400 can also include a system display 1440 that also illustrates various system operations 1442 set to occur, under normal working conditions across the time window. Operations 1442 of system display 1440 can differ from the operations illustrated in operations display 1430. In accordance with various embodiments, system operations 1442 can include operations that lock down the overall system until those associated tasks are performed. [DARSHAN: Operations 1442 can include, for example, a clean or full clean step, system diagnostics, etc. Similar to the operations display, system display 1440 can display various operations, depending on the progress of the workflow, including completed operations, in-process operations, and future operations. There are various ways to differentiate between completed, in-process and future operations. In FIG. 14A, these differences are illustrated by an associated color bar across the top of the operation. For example, completed operations can be represented by a blue bar, in-process operations by a green bar, and future operations by a white bar. Again, differentiation can take any form necessary to communicate completed from in-process and from future operations.

In accordance with various embodiments, GUI 1400 can also include one more nest operation displays 1450. The number of provided displays 1450 depends on the number of nests being utilized on the system. In FIG. 14A, there are four nest operations displays 1450. Similar to operations display 1430 and system display 1440, display 1450 can illustrate nest operations 1452 unique to one or more of the nest in use. Similar to the operations display, nest operations display 1450 can display various operations, depending on the progress of the workflow, including completed operations, in-process operations, and future operations. There are various ways to differentiate between completed, in-process and future operations. In FIG. 14A, these differences are illustrated by an associated color bar across the top of the operation. For example, completed operations can be represented by a blue bar, in-process operations by a green bar, and future operations by a white bar. Again, differentiation can take any form necessary to communicate completed from in-process and from future operations.

In accordance with various embodiments, GUI 1400 can also include one or more touchpoints 1460. Touchpoints 1460 can be provided, as shown in FIG. 14, horizontally along the workflow timeline. As discussed above, since automation is a critical component of advanced instrument platform, one key feature is to provide users the knowledge of when they will be expected to interact with the overall system through, for example, touchpoints 1460. To provide as efficient an automated and interactive system as possible, a software portion of the system can minimize the number of touchpoints. This can be done, for example by aggregating touchpoints to minimize user back and forth. Moreover, touchpoints can be brought forward where possible, particularly where the components of the instrument platform are in such a state to allow such aggregation and advancement.

Figure 14B:
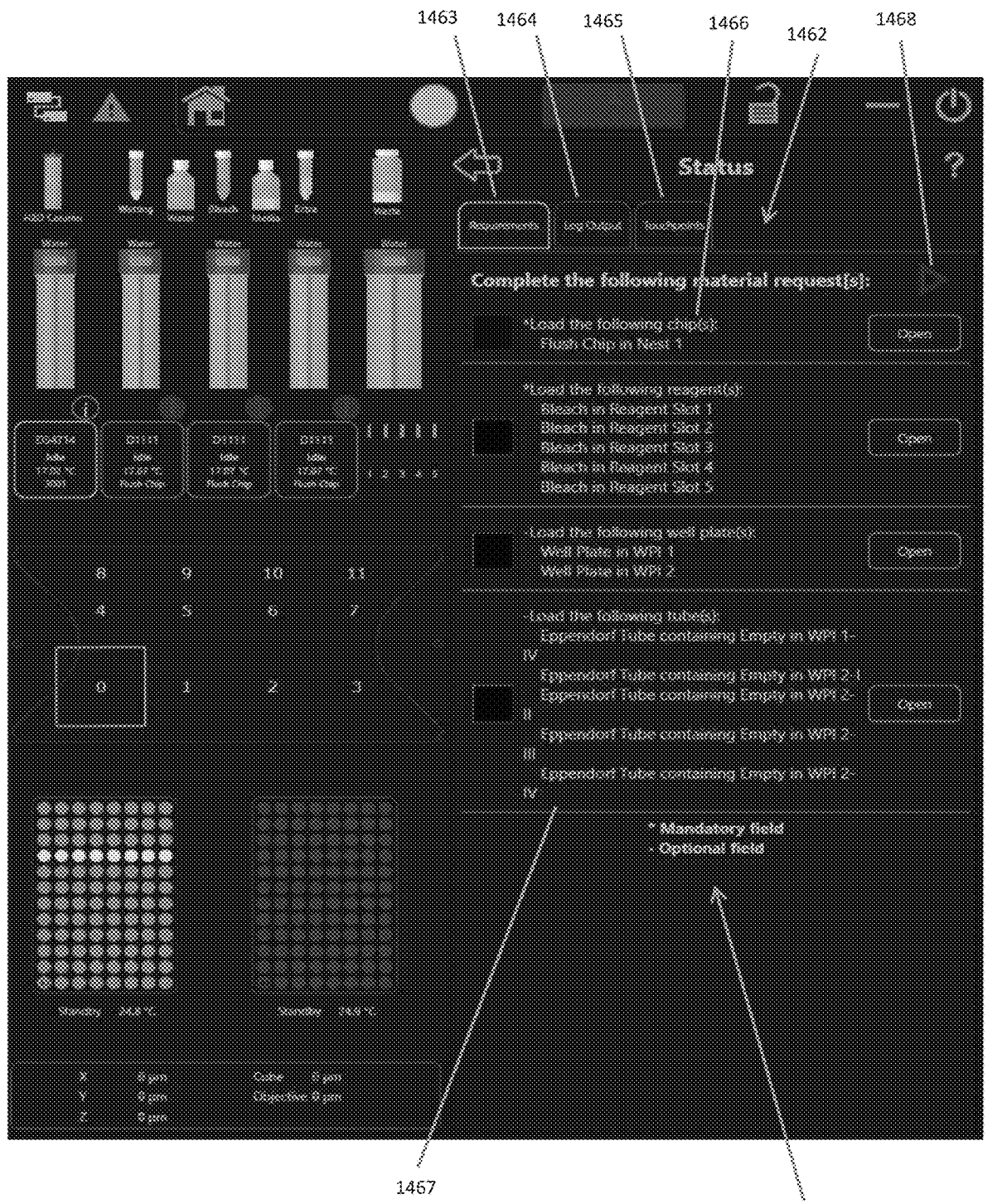

Referring to FIG. 14B, for each touchpoint 1460, one or more associated requirements 1461 can be provided in a status window 1462. The status window 1462 can include various tabs including, for example, a requirements tab 1463, a log output tab 1464 and a touchpoints tab 1465. The requirements 1461 can include fields for mandatory requirements 1466 and optional requirements 1467.

Regarding requirements 1461, any contemplated indicator can be used to differentiate mandatory requirements 1466 and optional requirements 1467. In FIG. 14B, for example, an "*" can be placed in proximity to the associated requirement (e.g., next to) to indicate a mandatory requirement and a "-" can be placed in proximity to the associated requirement (e.g., next to) to indicated an optional requirement. In FIG. 14B, for example, two mandatory requirements 1466 are provided and two optional requirements 1467 are provided. For example, the first mandatory requirement 1466 listed under the requirements tab 1463 requires the user to "Load the following chip(s): Flush Chip in Nest 1". For example, the first optional requirement 1467 listed under the requirements tab 1463 gives the user the option to "Load the following well plate(s): Well Plate in WPI 1 . . . Well Plate in WPI 2". Status window 1462 also includes a button 1468 that a user can click once requirements are met. In FIG. 14B, button 1468 is in the form of a sideways triangle (i.e., "play" button), though any contemplated button design can be considered.

Figure 14C:
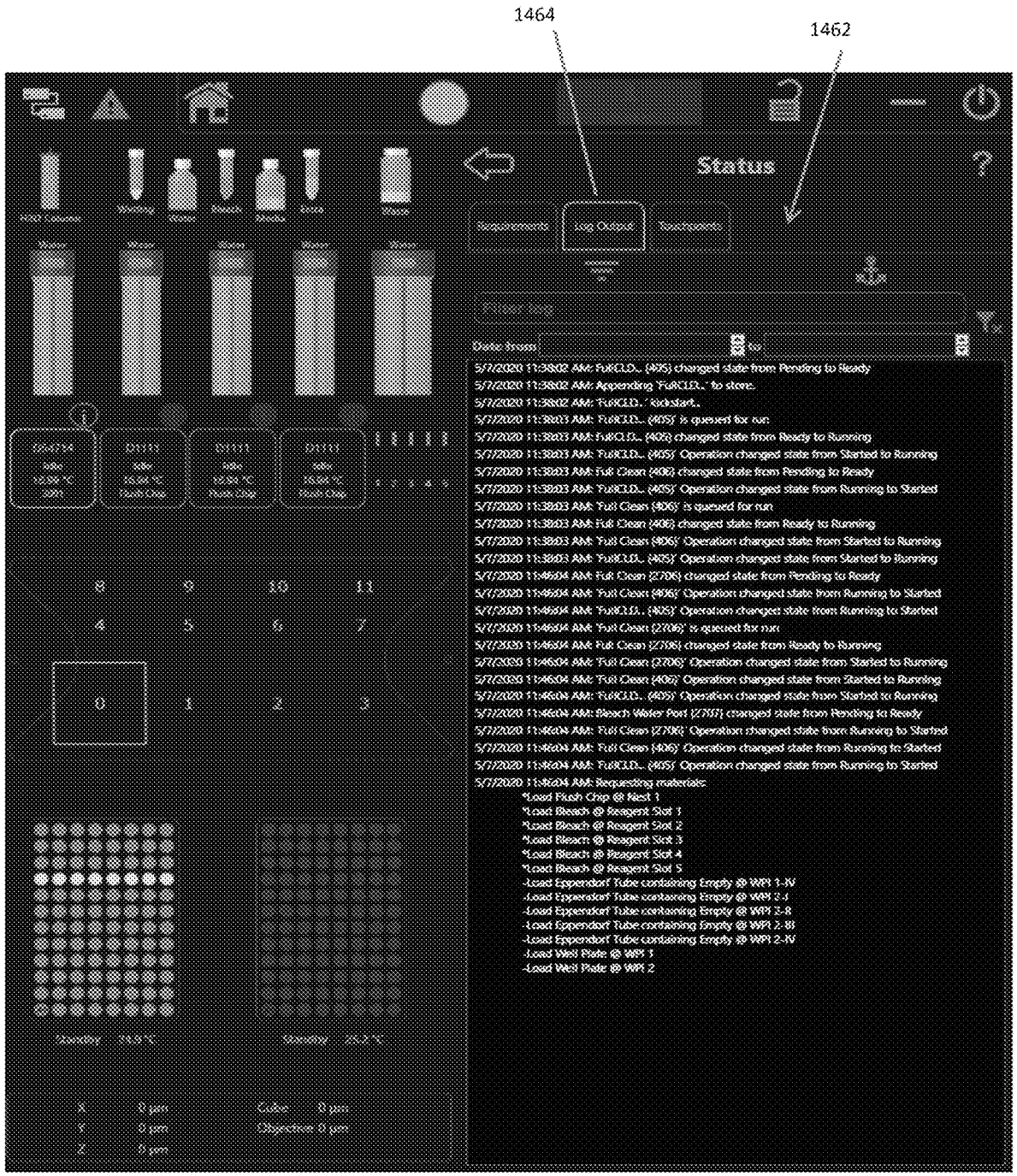

Referring now to FIG. 14C, the same display panel for GUI 1400 is shown as that shown in FIG. 14B. A notable distinction, however, is that FIG. 14C shows status window 1462 with the log output tab 1464 selected. As such, instead of a listing mandatory and/or optional requirements, as provided in FIG. 14B, a time-based log of all noted system operations, which can include, for example, request for materials, changes in operational states, and so on. Note that with the log output tab 1464 selected, button 1468 can be removed from the display. This can occur since, while within the log output tab 1464, no requirements are being read and no associated actions are required that would necessitate a button for clicking once requirements are met. Regarding the log, often the internal details of an operation are critical to likelihood of success or a user's understanding of the likelihood of success. The logs therefore capture such details, in addition to other events such as starts, stops, and completed events for an operation.

In accordance with various embodiments, the log tab can have a lock and search ability. The lock function can prevent the new events from forcing the view to scroll. The search function allows users to search for known text strings. Combined, these features and functions are very useful in determining what is occurring during a long workflow.

Figure 14D:
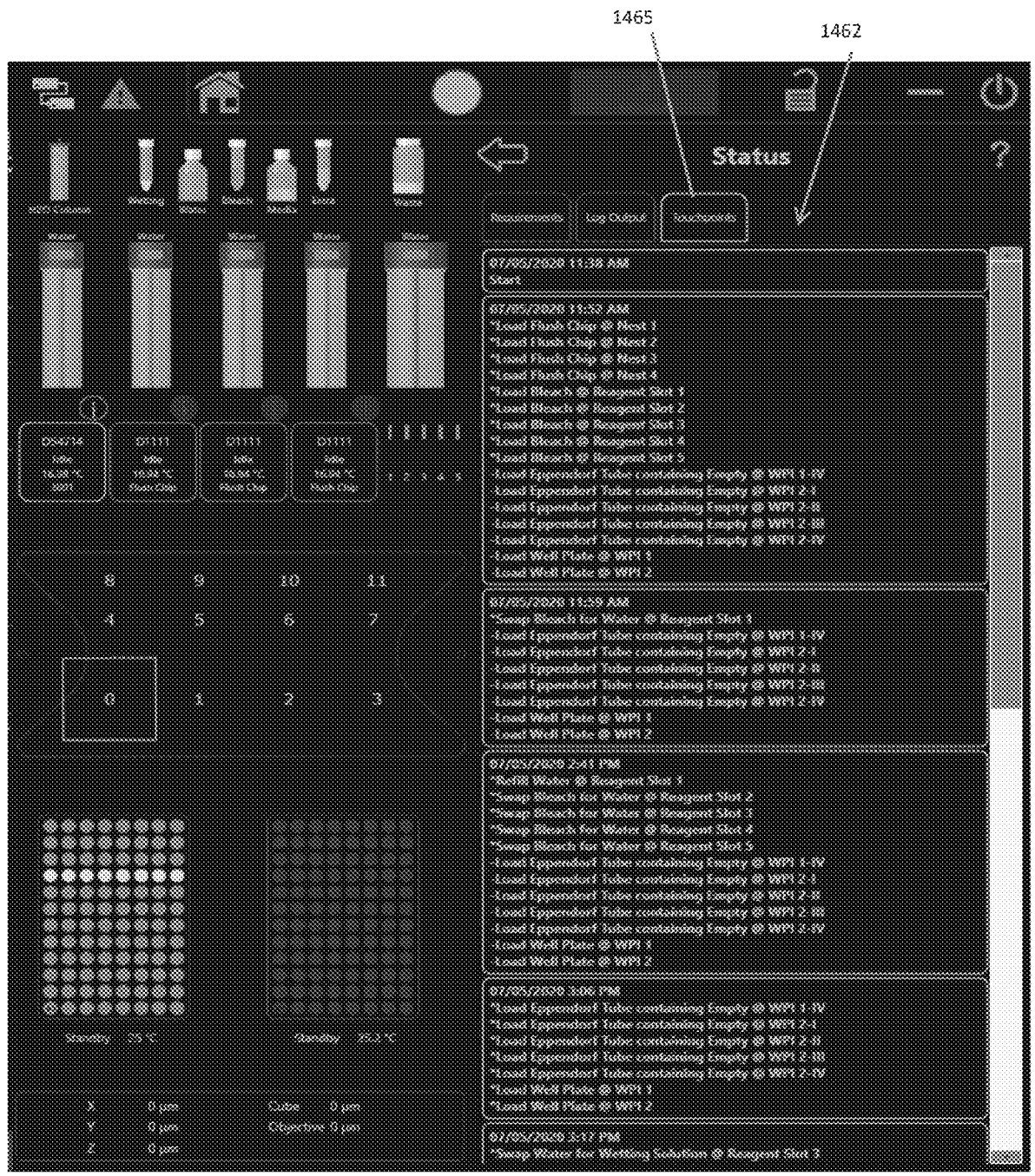

Referring now to FIG. 14D, the same display panel for GUI 1400 is shown as that shown in FIG. 14B. A notable distinction, however, is that FIG. 14D shows status window 1462 with the touchpoints tab 1465 selected. As such, instead of a listing mandatory and/or optional requirements, as provided in FIG. 14B, a list of all mandatory and/or optional requirements are listed. The list can be organized any number of ways. In FIG. 14D, the requirements are listed in chronological order. The number or scope of listed requirements can vary as needed or desired. In FIG. 14D, all requirements are listed for the entire workflow. Note again that with the touchpoints tab 1464 selected, button 1468 can be removed from the display. This can occur since, while within the touchpoints tab 1464, no requirements are being read and no associated actions are required that would necessitate a button for clicking once requirements are met.

In accordance with various embodiments, and as discussed previously, the GUI can include a time window (e.g., time window 1310 of FIG. 13A and time window 1410 of FIG. 14A). The time window can be configurable. The time window can be divided into any contemplated timeframe. For example, the timeframe displayed can be anywhere from five minutes to five days. In both FIGS. 13A and 14A, the time window is divided by days and displaying the entire five day protocol.

In accordance with various embodiments, the GUI can include a zoom feature that allows a full workflow to be viewed in segments of time within that workflow. As stated above, the zoom feature can provide workflow viewing down to as low as a five minute interval. The zoom feature provides numerous advantages including, for example, providing the user the ability to show more operational details that are not so easily viewed when the workflow timeline displayed is zoomed out to, for example, the full five days.

Figure 14E:
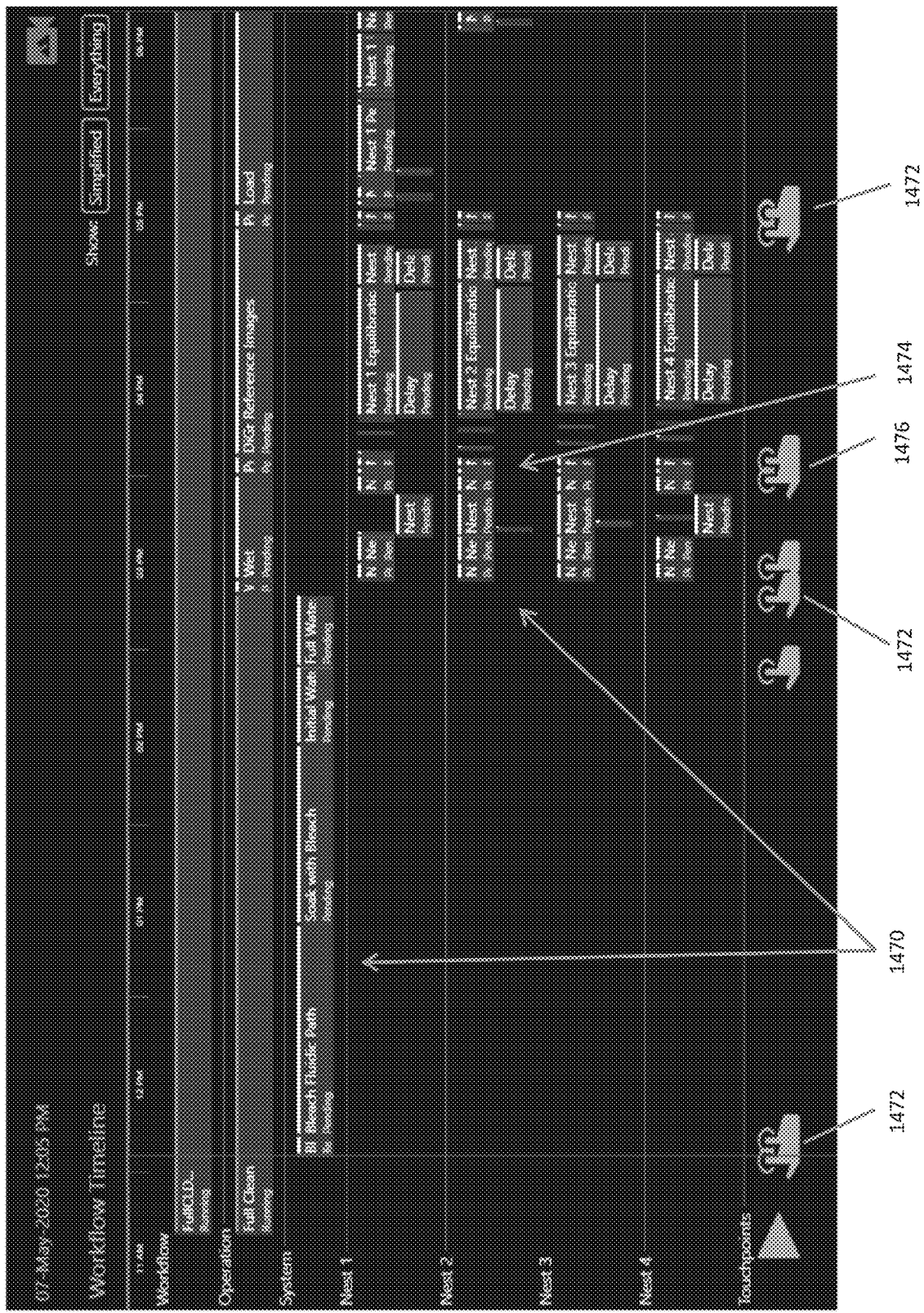

For example, FIG. 14E provides a zoomed in eight hour display (approximately) relative to the five day display of FIG. 14A. In comparing the two panels, it should be apparent that many of the operations occurring in the May 7 timeframe (first operations 1470) are not readily viewable and comprehendible based on those operations being so closely connected chronologically such that, at the zoomed out five day window of FIG. 14A, those operations appear stacked on each other. Similarly, the associated May 7 touchpoints, first touchpoints 1472, are stacked on each other as well. By comparison, when zoomed in to an approximate eight hour window of FIG. 14E, those same first operations 1470 are more readily viewable and comprehendible, and the associated first touchpoints 1472 are more readily distinguishable from each other rather than being stacked on each other as shown in FIG. 14A.

Figure 14F:
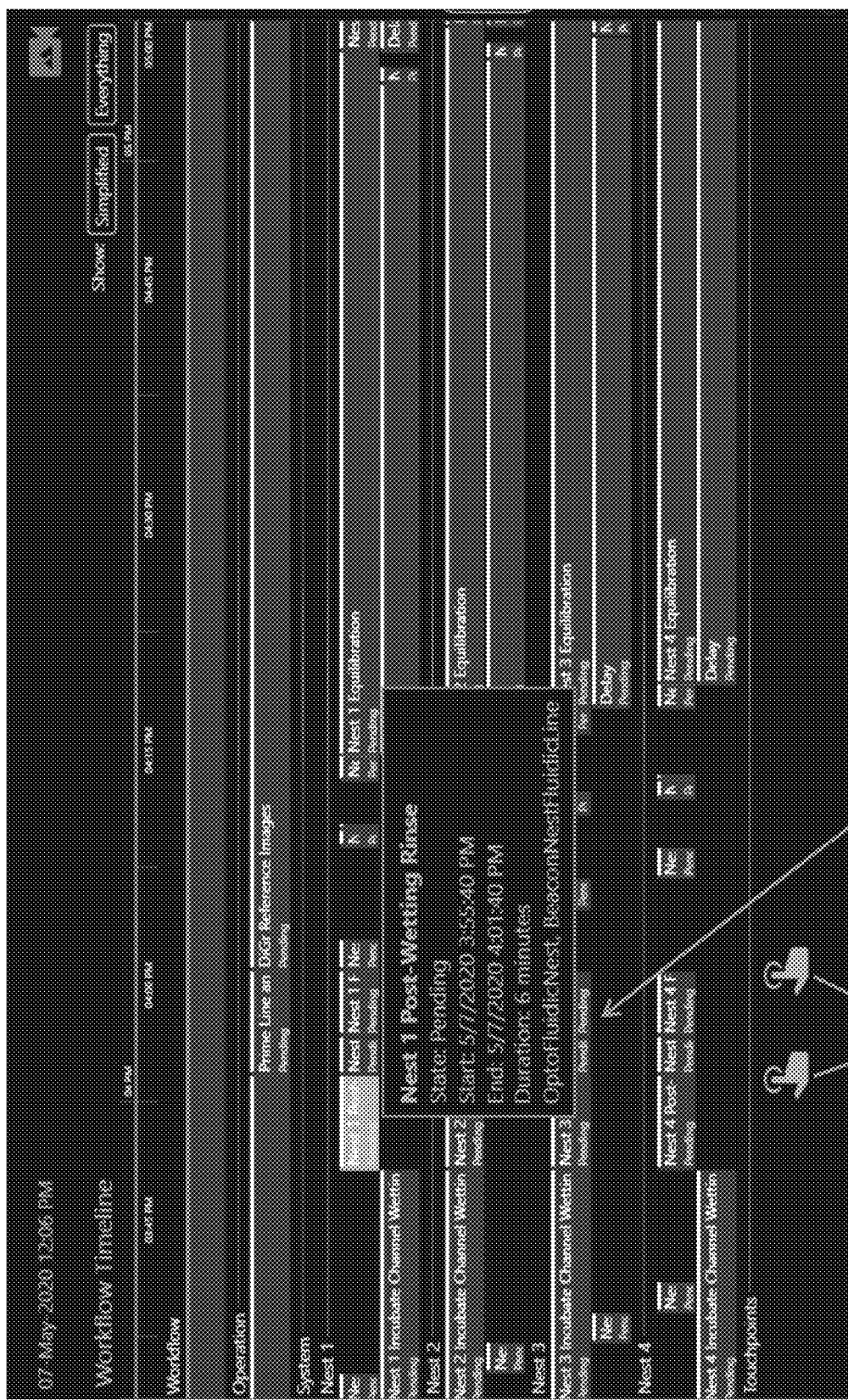
Figure 14G:
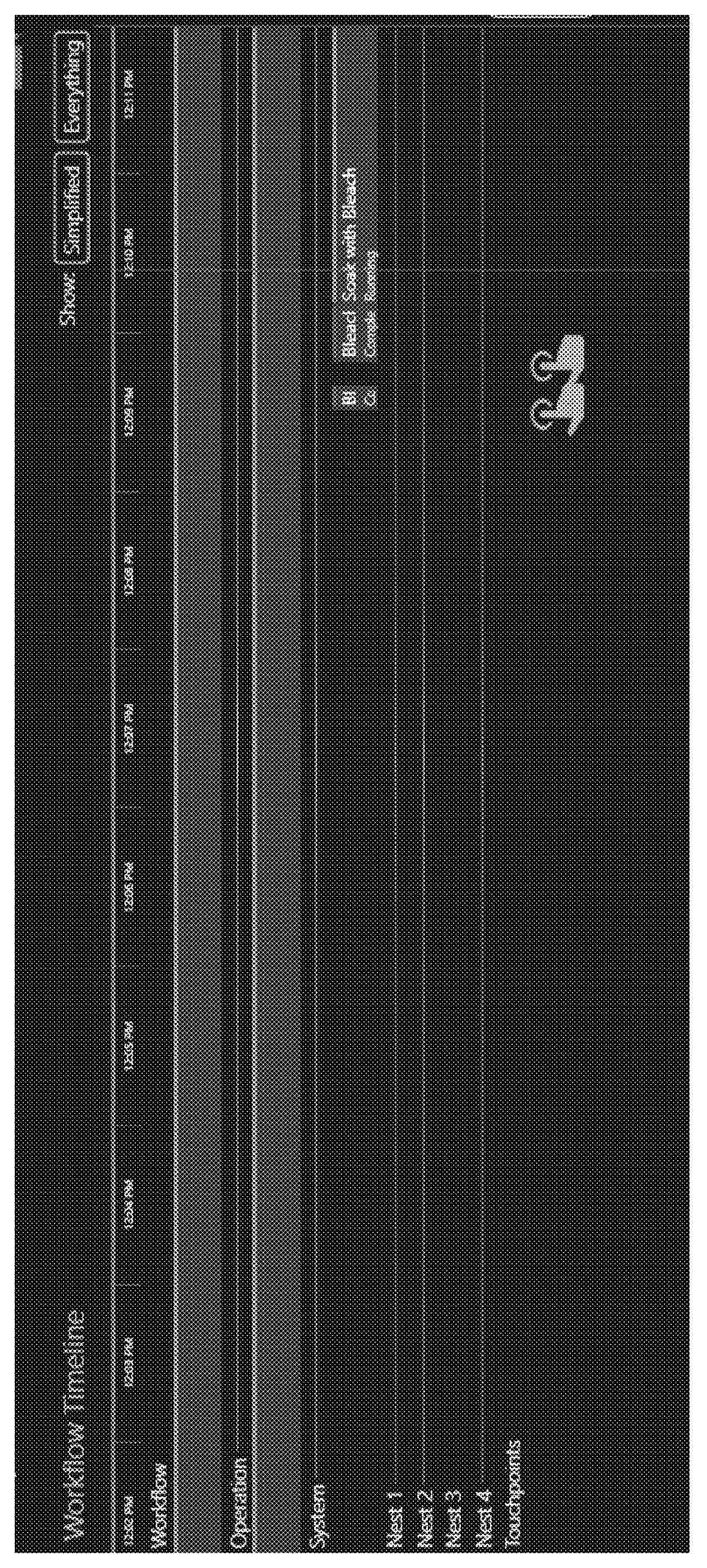

Further, FIG. 14F provides a zoomed in 90 minute display (approximately) relative to the five day display of FIG. 14A and the approximate eight hour display of FIG. 14E. When comparing a set of second operations 1474, and associated second touchpoints 1476, of FIG. 14E to the further zoomed in display of FIG. 14F, it again should be apparent that the second operations 1474, and associated second touchpoints 1476, and more readily viewable and comprehendible in FIG. 14F.

Further, FIG. 14G provides a zoomed in 10 minute display (approximately) relative to the five day display of FIG. 14A and the approximate 90 minute display of FIG. 14F. When comparing the timelines of FIG. 14F and FIG. 14G, it again should be apparent that operations and touchpoints should more readily viewable and comprehendible in FIG. 14F.

In accordance with various embodiments, the touchpoints displayed on the various GUIs can be impacted (i.e., changed, moved, combined or removed) by system features and performance aspects of the system overall. Combining that dynamic impact on the system with the overarching goal of minimizing touchpoints (to minimize necessary user supervision) by, for example, aggregating and bringing forward touchpoints where possible, the workflow can be dynamically and readily manipulated as needed. Various workflow factors can contribute to this manipulation. Examples of workflow factors include levels of those reagents that are fed into the system, levels of deionized water that are fed into the system, levels of bleach that are fed into the system, the types and number of chips used in the system nests, the number of nests used in the workflow, and the presence/absence of well plates in the well plate incubators (both presence and absence can be desired depending on the point in the workflow). It should be noted that the type of factors and types of requirements provided above are examples only. The interrelation of any and all workflow operations, the associated requirements, and associated touchpoints, is applicable for any requirement type or material requirement.

Depending on the status of these factors (e.g., levels, numbers, types, presence, absence, etc.) versus expectations, these factors can lead to the re-computing of touchpoints to maximize efficiency of the system, ensure the workflow progresses, and minimize user supervision of the workflow. This re-computing can occur in real-time leading to a dynamic display of the workflow status, with a single occurrence in the system potentially altering the workflow in real-time, and also changing when and how often a user must interact with the system. Touchpoints can be re-computed for various reasons including. For example, Touchpoints can be re-computed when the workflow first starts. Touchpoints can be re-computed when an active prompt blocks the workflow, thus leading to touchpoint re-computing once the prompt is satisfied, generally leading to the movement of touchpoints in the timeline. Touchpoints can be re-computed when the workflow encounters an error and is waiting for user to intercede, thus leading to touchpoint re-computing once the prompt is satisfied, generally leading to the movement of touchpoints in the timeline. Touchpoints can be re-computed when a user stops and restarts any operation, with such actions prompting re-computing upon restart. Touchpoints can be re-computed for periodic operations, which may require repeated action over a specific time window (e.g., performing an action between two and 20 times in a five minute window). In this case, each periodic operation can prompt re-computation. Touchpoints can be re-computed when something occurs on the system that can necessitate the addition or subtraction of operations in real-time, thus leading to re-computation.

In accordance with various embodiments, a graphical user interface (GUI) for dynamically displaying experimental workflow conditions is provided. The GUI can comprise a configurable time window providing a time range equal to or less than the time needed to execute the experimental workflow. The GUI can further comprise a workflow display providing overall status of the experimental workflow within the time window, an operations display providing workflow operations within the time window, and a current time indicator providing a visual representation of the current time within the time window. The GUI can further comprise a requirement associated with the current time indicator and a touchpoint image associated with the requirement, wherein the requirement is manipulated in real-time during the workflow in response to one or more workflow factors impacting the system operations within the time window, and wherein the touchpoint image is automatically re-positioned in response to the manipulation of the requirement.

In accordance with various embodiments, the manipulation of the requirement can include removing the requirement, adding one or more additional requirements, advancing the requirement in the time window, pushing back the requirement in the time window, reframing the requirement, or a combination thereof. The reframing of the requirement can include changing the content of the requirement or changing the label of the requirement. The requirement can be assigned a label of mandatory requirement or optional requirement, and the label can be changed in response to the one or more workflow factors impacting the system operations.

In accordance with various embodiments, the GUI can further include a system display providing system operations within the time window.

In accordance with various embodiments, the GUI can further comprise a nest operations display providing nest operations within the time window. The nest operations display can provide from one to four individual nest displays, and display nest operations specific to each individual nest display.

In accordance with various embodiments, the GUI can further comprise a status window that provides a selectable tab selected from the group consisting of a requirements tab, a log output tab, a touchpoints tab, and combinations thereof. The requirements tab can display a listing of one or more textual frames with information about the requirements associated with the current time indicator. Moreover, the information can be manipulated in real-time in response manipulation of the associated requirements in response to one or more workflow factors impacting the system operations within the time window. Further, each textual frame can be associated with a single requirement.

In accordance with various embodiments, the listing of one or more textual frames can comprise two or more textual frames. The listing of one or more textual frames can comprise three or more textual frames.

In accordance with various embodiments, the time window can be configured between about five minutes and about five days. The time window can be configured using a selectable zoom feature on the GUI.

In accordance with various embodiments, the workflow display, operations display, and touchpoint image can be automatically repositioned on the GUI in response to a change to the time window.

In accordance with various embodiments, the workflow display, operations display, system display, and touchpoint image can be automatically repositioned on the GUI in response to a change to the time window.

In accordance with various embodiments, the workflow display, operations display, system display, nest operations display, and touchpoint image can be automatically repositioned on the GUI in response to a change to the time window.

In accordance with various embodiments, the one or more factors can be selected from the group consisting of reagent levels, deionized water levels, bleach levels, chip types used in the workflow, the number of chips used in the workflow, the number of nests used in the workflow, the presence of well plates in well plate incubators, the absence of well plates in well plate incubators, and combinations thereof.

In accordance with various embodiments, the GUI of can further comprise a plurality of requirements associated with the current time indicator, and a touchpoint image associated with each of the plurality of requirements.

In accordance with various embodiments, the workflow operations can be categorized as a completed operation, an in-process operation, or a future operation. The workflow operations can be displayed such that each category of operation can be visually distinguished from the other categories. Each category can be provided a specific color such that each category of operation can be visually distinguished from the other categories.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The invention also relates to a device or an apparatus for performing these operations. The systems and methods described herein can be specially constructed for the required purposes, such as the carrier network discussed above, or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

The embodiments described herein can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CDRWs, magnetic tapes, and other optical and non-optical data storage devices. The computer readable medium can also be distributed over a network coupled computer systems so that the computer readable code is stored and executed in a distributed fashion.

Although a few embodiments of the present invention have been described in detail herein, it should be understood, by those of ordinary skill, that the present invention may be embodied in many other specific forms without departing from the spirit or scope of the invention. Therefore, the present examples and embodiments, including the PARTIAL LISTING OF EMBODIMENTS presented below, are to be considered as illustrative and not restrictive, and the invention is not to be limited to the details provided therein, but may be modified and practiced within the scope of the appended claims.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Partial Listing of Embodiments

Embodiment 1

A system for dynamically optimizing an instrument system workflow, the system comprising: one or more instrument resources, each resource with an instrument resource sensor (e.g., a dedicated instrument resource sensor) configured to acquire data from the instrument resource; one or more sample chambers, each sample chamber with a sample chamber sensor (e.g., dedicated sample chamber sensor) configured to acquire data from the sample chamber; and a computing device communicatively connected to the one or more instrument resources (or sensors thereof) and sample chambers (or sensors thereof), the computing device comprising: a workflow builder configured to allow a user to create/customize an instrument workflow program for an instrument system; a virtual system modeling engine configured to optimize the instrument workflow program utilizing a virtual system model of the instrument system and generate an optimized instrument workflow program; an analytics engine communicatively connected to the instrument resource sensor(s) and sample chamber sensor(s) and configured to monitor real-time data output from the instrument resource sensor(s) and sample chamber sensor(s), and initiate a calibration operation to update the virtual system model when a variance condition is detected in the data output from at least one of the instrument resource sensor(s) and sample chamber sensor(s); and an execution engine configured to process the optimized instrument workflow program for the instrument system and provide operating instructions to the one or more instrument resources and sample chambers.

Embodiment 2

The system of Embodiment 1, further comprising: a machine learning engine configured to train the analytics engine to further improve the optimized instrument workflow program.

Embodiment 3

The system of Embodiment 1 or 2, wherein the one or more instrument resources comprises a pump, a nest, a needle, or a receptacle.

Embodiment 4

The system of any one of Embodiments 1 to 3, wherein the one or more sample chambers comprises an incubator, a well plate, and/or a sample tube.

Embodiment 5

The system of any one of Embodiments 1 to 4, wherein the one or more instrument resources and the one or more sample chambers are housed within a housing.

Embodiment 6

The system of any one of Embodiments 1 to 4, wherein the one or more instrument resources, the one or more sample chambers, and the computing device are housed within a housing.

Embodiment 7

The system of any one of Embodiments 1 to 6, wherein the computing device is configured to receive user input.

Embodiment 8

The system of any one of Embodiments 1 to 7, wherein the variance condition includes an alarm from the sensors, a warning of low material detected by the sensors, a result of a periodic image analysis, an end of workflow step notification, or a user input (e.g., a command alters the instrument workflow program).

Embodiment 9

The system of any one of Embodiments 1 to 8, wherein the resource sensor and chamber sensor data is acquired in real-time.

Embodiment 10

A method for dynamically optimizing an instrument system workflow, the method comprising: creating an instrument workflow program comprising one or more operating instructions for an instrument resource and a sample chamber (e.g., the instrument resource and the sample chamber may be housed in an instrument system); acquiring data from sensors monitoring the instrument resource and sample chamber; updating a virtual system model of the instrument system in response to detecting a variance condition in the acquired data; generating, as needed, an optimized instrument workflow program utilizing the updated virtual system model; and providing operating instructions to the instrument resource and sample chamber based on the instrument workflow program (or optimized instrument workflow program).

Embodiment 11

The method of Embodiment 10, further comprising: improving the virtual system model utilizing machine learning; and generating a further optimized instrument workflow program utilizing the improved virtual system model.

Embodiment 12

The method of Embodiment 10 or 11, wherein the instrument resource comprises a pump, a nest, a needle, or a receptacle.

Embodiment 13

The method of any one of Embodiments 10 to 12, wherein the sample chamber comprises an incubator, a well plate, and/or a sample tube.

Embodiment 14

The method of any one of Embodiments 10 to 13, wherein the instrument resource (or sensor thereof) and the sample chamber (or sensor thereof) are communicatively coupled to a computer device via a network connection.

Embodiment 15

The method of any one of Embodiments 10 to 13, wherein the instrument system comprises a computing device that is communicatively coupled to the instrument resource (or sensor thereof) and the sample chamber (or sensor thereof).

Embodiment 16

The method of any one of Embodiments 10 to 15, wherein updating the virtual system model includes updating periodically at a preset interval.

Embodiment 17

The method of any one of Embodiments 10 to 16, wherein the computing device is configured to receive user input.

Embodiment 18

The method of any one of Embodiments 10 to 17, wherein the variance condition includes an alarm from one or more of the sensors, a warning of low material detected by one or more of the sensors, a result of a periodic image analysis, an end of workflow step notification, or a user input (e.g., a command that alters the instrument workflow program).

Embodiment 19

The system of any one of Embodiments 1 to 7, wherein the resource sensor and chamber sensor data is acquired in real-time.

Embodiment 20

A non-transitory machine-readable storage medium comprising machine-readable instructions for causing a processor to execute a method for dynamically optimizing an instrument system workflow, comprising: creating an instrument workflow program comprising one or more operating instructions for an instrument resource and a sample chamber (e.g., the instrument resource and the sample chamber may be housed in an instrument system); acquiring data from sensors monitoring the instrument resource and sample chamber; updating a virtual system model of the instrument system in response to detecting a variance condition in the acquired data; generating, as needed, an optimized instrument workflow program utilizing the updated virtual system model; and providing operating instructions to the instrument resource and sample chamber based on the instrument workflow program (or optimized instrument workflow program).

Embodiment 21

The non-transitory machine-readable storage medium of Embodiment 20, wherein the method further comprises: improving the virtual system model (or updated virtual system model) utilizing machine learning; and generating a further optimized instrument workflow program utilizing the improved virtual system model (or improved updated virtual system model).

Embodiment 22

The non-transitory machine-readable storage medium of Embodiment 20 or 21, wherein the instrument resource comprises a pump, a nest, a needle, or a receptacle.

Embodiment 23

The non-transitory machine-readable storage medium of any one of Embodiments 20 to 22, wherein the sample chamber comprises an incubator, a well plate, and/or a sample tube.

Embodiment 24

The non-transitory machine-readable storage medium of any one of Embodiments 20 to 23, wherein the instrument resource (or sensor thereof) and the sample chamber (or sensor thereof) are communicatively coupled to a computer device via a network connection.

Embodiment 25

The non-transitory machine-readable storage medium of any one of Embodiments 20 to 23, wherein the instrument system comprises a computing device that is communicatively coupled to the instrument resource (or sensor thereof) and the sample chamber (or sensor thereof).

Embodiment 26

The non-transitory machine-readable storage medium of any one of Embodiments 20 to 25, wherein updating the virtual system model includes updating periodically at a preset interval.

Embodiment 27

The non-transitory machine-readable storage medium of any one of Embodiments 20 to 26, wherein the variance condition includes an alarm from one or more of the sensors, a warning of low material detected by one or more of the sensors, a result of a periodic image analysis, or an end of workflow step notification.

Embodiment 28

A system for dynamically optimizing an instrument system workflow, the system comprising: one or more instrument resources and at least one instrument resource sensor configured to acquire data from one or more of the instrument resource(s); a holder for a sample chamber and at least one sample chamber sensor; one or more receptacles, each receptacle configured to hold a reagent; and a computing device communicatively connected to each of the one or more instrument resources and/or their sensor(s) and each of the one or more sample chambers and/or their sensor(s), the computing device comprising: a workflow builder configured to accept user input and create a workflow program to be performed by the instrument system, wherein the workflow program comprises a series of operations, wherein each operation of the series may be selected and/or configured by the user; an operations framework configured to direct the performance of the workflow program by the instrument system by calling each operation in the series of operations, wherein timing of the calling of operations is adjusted based on data received from the at least one instrument resource sensor, the at least one sample chamber sensor, at least one operation, and/or additional user input to thereby optimize time to completion of the workflow program; a set of operations, each operation configured to instruct one or more instrument resources to perform a predetermined task; and a workflow modeling component configured to receive data from the operations framework and, optionally, one or more operations in the series of operations, and maintain a model of the status of the workflow program based upon the received data.

Embodiment 29

The system of Embodiment 28 further comprising: a machine learning engine configured to work with the operations framework to improve the timing of the calling of operations and thereby further optimize the time to completion of the workflow program.

Embodiment 30

The system of Embodiment 28 or 29, wherein the operations framework adjusts the calling of operations in real time.

Embodiment 31

The system of any one of Embodiments 28 to 30, wherein each of the one or more instrument resources comprises a pump, an input/output needle, an incubator, a holder for a sample chamber, a stage, or an optical train.

Embodiment 32

The system of Embodiment 31, wherein the system comprises an incubator, and wherein the incubator is configured to hold a well plate.

Embodiment 33

The system of any one of Embodiments 28 to 32, wherein the system comprises a plurality of instrument resources.

Embodiment 34

The system of Embodiment 33, wherein each of the plurality of instrument resources has an instrument resource sensor configured to acquire data from the instrument resource.

Embodiment 35

The system of Embodiment 33, wherein each of the plurality of instrument resources has a dedicated instrument resource sensor configured to acquire data from the instrument resource.

Embodiment 36

The system of any one of Embodiments 28 to 35, wherein the sample chamber holder is a nest and the sample chamber is a microfluidic device.

Embodiment 37

The system of Embodiment 36, wherein the nest comprises electrical and fluidic connections for interfacing with the microfluidic device.

Embodiment 38

The system of any one of Embodiments 28 to 37, wherein the system comprises a plurality of sample chamber holders.

Embodiment 39

The system of any one of Embodiment 28 to 38, wherein the at least one sample chamber sensor comprises an optical train, and wherein the optical train comprises a camera configured to image the sample chamber.

Embodiment 40

The system of Embodiment 39, wherein the optical train further comprises a projector and/or a laser.

Embodiment 41

The system of any one of Embodiments 28 to 40, wherein the system comprises a plurality of receptacles.

Embodiment 42

The system of any one of Embodiments 28 to 41, wherein the system further comprises one or more holders for sample containers used to hold pre-processed or post-processed sample.

Embodiment 43

The system of Embodiment 42, wherein the sample container holders are configured to hold a tube or a well plate.

Embodiment 44

The system of any one of Embodiments 28 to 43, wherein data received by the operations framework from the at least one (e.g., a first) instrument resource sensor is received directly from the instrument resource sensor.

Embodiment 45

The system of any one of Embodiments 28 to 44, wherein data received by the operations framework from the at least one (e.g., a second) instrument resource sensor is received indirectly from an operation that instructed the corresponding instrument resource.

Embodiment 46

The system of any one of Embodiments 28 to 45, wherein the additional user input received by the operations framework is received indirectly from the workflow modeling component.

Embodiment 47

The system of any one of Embodiments 28 to 46, wherein the set of operations comprises operations for loading a sample into the sample chamber, detecting micro-objects located within the sample chamber, relocating micro-objects detected in the sample chamber, supplying one or more reagents to the sample chamber, assaying micro-objects detected in the sample chamber, and exporting micro-objects from the sample chamber.

Embodiment 48

The system of any one of Embodiments 28 to 47, wherein the workflow modeling component maintains a real time model of the status of the workflow program based upon the received data.

Embodiment 49

The system of any one of Embodiments 28 to 48, wherein the model of the status of the workflow program maintained by the workflow modeling component is displayed on a graphical user interface, wherein the workflow modeling component is further configured to instruct the user to perform specific tasks during the performance of the workflow program.

Embodiment 50

The system of any one of Embodiments 28 to 49, wherein the workflow modeling component is further configured to request additional user input during the performance of the workflow program, wherein the additional user input is passed along to the operations framework.

Embodiment 51

The system of any one of Embodiments 28 to 50, wherein the data received by the operations framework comprises an alarm indicating that a one or more operations in the series of operations cannot be completed, a warning of low material detected in the one or more receptacles, a result from an analysis of an image of the sample chamber, completion of an operation in the series of operations, or a user input (e.g., a command that alters the workflow program).

Embodiment 52

The system of any one of Embodiments 28 to 51, wherein the one or more instrument resources, the sample chamber holder, and the one or more receptacles are housed within a housing.

Embodiment 53

The system of any one of Embodiments 28 to 51, wherein the one or more instrument resources, the sample chamber holder, the one or more receptacles, and the computing device are housed within a housing.

Embodiment 54

A method for dynamically optimizing an workflow program, the method comprising: creating a workflow program comprising a series of operations, each operation of the series comprising operating instructions for one or more instrument resources housed in an instrument system; acquiring data from sensors monitoring the one or more instrument resources and a sample chamber comprising a sample; generating an optimized workflow program in response to detecting a variance condition in the acquired data; utilizing the optimized workflow program to update a model of the status of the workflow program; and providing operating instructions to the one or more instrument resources based on the optimized instrument workflow program.

Embodiment 55

The method of Embodiment 55, wherein the instrument system is the system of any one of Embodiments 28 to 53.

Embodiment 56

The method of Embodiment 55 or 56 further comprising: improving the generation of the optimized workflow program by application of a machine learning algorithm.

Embodiment 57

The method of any one of Embodiments 54 to 56, wherein each of the one or more instrument resources comprises a pump, an input/output needle, an incubator, a holder for a sample chamber, a stage, or an optical train.

Embodiment 58

The method of any one of Embodiments 54 to 57, wherein the sample chamber is held by a nest and the sample chamber is a microfluidic device.

Embodiment 59

The method of Embodiment 58, wherein the nest comprises electrical and fluidic connections for interfacing with the microfluidic device.

Embodiment 60

The method of any one of Embodiments 54 to 59, wherein the method is performed on a plurality of sample chambers.

Embodiment 61

The method of any one of Embodiments 54 to 60, wherein the sensors monitoring the one or more instrument resources and the sample chamber are communicatively coupled to a computer device via a network connection.

Embodiment 62

The method of any one of Embodiments 54 to 61, wherein the instrument system comprises a computing device that is communicatively coupled to the sensors monitoring the one or more instrument resources and the sample chamber.

Embodiment 63

The method of any one of Embodiments 54 to 62, wherein updating the model of the status of the workflow program is performed periodically, optionally at a preset interval.

Embodiment 64

The method of any one of Embodiments 54 to 63, wherein the variance condition comprises an alarm indicating that one or more operations in the series of operations cannot be completed, a warning of low material detected in an instrument system receptacle, a result from an analysis of an image of the sample chamber, completion of an operation in the series of operations, or a user input (e.g., a command that alters the workflow program).

Embodiment 65

A non-transitory machine-readable storage medium comprising machine-readable instructions for causing a processor to execute a method for dynamically optimizing an workflow program, the method comprising: creating a workflow program comprising a series of operations, each operation comprising operating instructions for one or more instrument resources housed in an instrument system; acquiring data from sensors monitoring the one or more instrument resources and a sample chamber comprising a sample; generating an optimized workflow program in response to detecting a variance condition in the acquired data; utilizing the optimized workflow program to update a model of the status of the workflow program; and providing operating instructions to the one or more instrument resources based on the optimized instrument workflow program.

Embodiment 66

The non-transitory machine-readable storage medium of Embodiment 65, wherein the instrument system is the system of any one of Embodiments 28 to 53.

Embodiment 67

The non-transitory machine-readable storage medium of Embodiment 65 or 66, wherein the method comprises improving the generation of the optimized workflow program by application of a machine learning algorithm.

Embodiment 68

The non-transitory machine-readable storage medium of any one of Embodiments 65 to 67, wherein each of the one or more instrument resources comprises a pump, an input/output needle, an incubator, a holder for a sample chamber, a stage, or an optical train.

Embodiment 69

The non-transitory machine-readable storage medium of any one of Embodiments 65 to 68, wherein the sample chamber is held by a nest and the sample chamber is a microfluidic device.

Embodiment 70

The non-transitory machine-readable storage medium of Embodiment 69, wherein the nest comprises electrical and fluidic connections for interfacing with the microfluidic device.

Embodiment 71

The non-transitory machine-readable storage medium of any one of Embodiments 65 to 70, wherein the method is performed on a plurality of sample chambers.

Embodiment 72

The non-transitory machine-readable storage medium of any one of Embodiments 65 to 71, wherein the sensors monitoring the one or more instrument resources and the sample chamber are communicatively coupled to a computer device via a network connection.

Embodiment 73

The non-transitory machine-readable storage medium of any one of Embodiment 65 to 72, wherein the instrument system comprises a computing device that is communicatively coupled to the sensors of the one or more instrument resources and the sample chamber.

Embodiment 74

The non-transitory machine-readable storage medium of any one of Embodiments 65 to 73, wherein updating the model of the status of the workflow program is performed periodically, optionally at a preset interval.

Embodiment 75

The non-transitory machine-readable storage medium of any one of Embodiments 65 to 74, wherein the variance condition comprises an alarm indicating that one or more operations in the series of operations cannot be completed, a warning of low material detected in an instrument system receptacle, a result from an analysis of an image of the sample chamber, completion of an operation in the series of operations, or a user input (e.g., a command that alters the workflow program).

Embodiment 76

A graphical user interface (GUI) for dynamically displaying experimental workflow conditions, the GUI comprising: a configurable time window providing a time range equal to or less than the time needed to execute the experimental workflow; a workflow display providing overall status of the experimental workflow within the time window; an operations display providing workflow operations within the time window; a current time indicator providing a visual representation of the current time within the time window; and one or more touchpoint images indicating times during the experimental workflow when a user will need to interact with a system performing the experimental workflow, wherein each touchpoint image is associated with a requirement, wherein the requirement is manipulated in real-time during the workflow in response to one or more workflow factors impacting the system operations within the time window, and wherein the corresponding touchpoint image is automatically re-positioned in response to the manipulation of the requirement.

Embodiment 77

The GUI of Embodiment 76, wherein the manipulation of the requirement includes removing the requirement, adding one or more additional requirements, advancing the requirement in the time window, pushing back the requirement in the time window, reframing the requirement, or a combination thereof.

Embodiment 78

The GUI of Embodiment 77, wherein reframing the requirement includes changing the content of the requirement or changing the label of the requirement.

Embodiment 79

The GUI of any one of Embodiments 76 to 78, wherein the requirement is assigned a label of mandatory requirement or optional requirement, and wherein the label is changed in response to the one or more workflow factors impacting the system operations.

Embodiment 80

The GUI of any one of Embodiments 76 to 79, further comprising a system display providing system operations within the time window.

Embodiment 81

The GUI of any one of Embodiments 76 to 80, further comprising a nest operations display providing nest operations within the time window.

Embodiment 82

The GUI of Embodiment 81, wherein the nest operations display provides a plurality (e.g., 2, 3, 4, or more) individual nest displays, each nest display of the plurality displaying nest operations specific to a corresponding nest of the system.

Embodiment 83

The GUI of any one of Embodiments 76 to 82, further comprising a status window that provides a plurality of selectable tabs, the plurality of selectable tags including a requirements tab, a log output tab, a touchpoints tab, or any combination thereof.

Embodiment 84

The GUI of Embodiment 83, wherein the requirements tab displays a listing of one or more textual frames with information about upcoming (or pending) requirements associated with at least one of the one or more touchpoint images, and wherein the one or more textual frames are manipulated in real-time in response to manipulation of the associated workflow requirements in response to one or more workflow factors impacting the system operations.

Embodiment 85

The GUI of Embodiment 84, wherein each textual frame is associated with a single requirement.

Embodiment 86

The GUI of Embodiment 84 or 85, wherein the listing of one or more textual frames comprises two or more textual frames.

Embodiment 87

The GUI of Embodiment 84 or 85, wherein the listing of one or more textual frames comprises three or more textual frames.

Embodiment 88

The GUI of any one of Embodiments 76 to 87, wherein the time window is configured between about five minutes and about one week.

Embodiment 89

The GUI of any one of Embodiments 76 to 88, wherein the time window is configured using a selectable zoom feature on the GUI.

Embodiment 90

The GUI of any one of Embodiments 76 to 89, wherein the workflow display, the operations display, and the one or more touchpoint images are automatically repositioned on the GUI in response to a change to the time window.

Embodiment 91

The GUI of any one of Embodiments 76 to 89, wherein the workflow display, the operations display, a (the) system display, and the one or more touchpoint images are automatically repositioned on the GUI in response to a change to the time window.

Embodiment 92

The GUI of any one of Embodiments 76 to 89, wherein the workflow display, the operations display, a (the) system display, a (the) nest operations display, and the one or more touchpoint images are automatically repositioned on the GUI in response to a change to the time window.

Embodiment 93

The GUI of any one of Embodiments 76 to 92, further comprising a display of one or more reagent levels, deionized water level, bleach level, number of chips (e.g., microfluidic chips) used in the workflow, type of chip(s) used in the workflow (e.g., serial number and/or chip design), number of nests used in the workflow, presence of well plates in well plate incubators, absence of well plates in well plate incubators, and any combination thereof.

Embodiment 94

The GUI of any one of Embodiments 76 to 93, further comprising a plurality of touchpoint images and, optionally,

39 one or more requirements associated with each of the plurality of touchpoint images.

Embodiment 95

The GUI of any one of Embodiments 76 to 94, wherein the workflow operations are categorized as a completed operation, an in-process operation, or a future operation.

Embodiment 96

The GUI of Embodiment 95, wherein the workflow operations are displayed such that each category of workflow operation is visually distinguished from the other categories.

Embodiment 97

The GUI of Embodiment 96, wherein each category of workflow operation is provided a specific color and/or pattern such that each category of operation is visually distinguished from the other categories.

What is claimed is:

1. A system for dynamically updating an instrument system workflow, comprising:
   an instrument system comprising a plurality of hardware components, the plurality of hardware components comprising:
     one or more instrument resources, each instrument resource having an instrument resource sensor configured to acquire data from the instrument resource;
     one or more sample chambers, each sample chamber having a sample chamber sensor configured to acquire data from the sample chamber; and
   a computing device communicatively connected to the instrument resources and the sample chambers, or the sensors thereof, the computing device configured to execute software components comprising:
     a workflow builder comprising software instructions which, when executed by the computing device, allow a user to create or customize an instrument workflow program comprising software instructions configured for execution by the instrument system;
     a virtual system modeling engine comprising software instructions which, when executed by the computing device, update the instrument workflow program utilizing a model of the instrument system and generate an updated instrument workflow program comprising software instructions which, when executed by the computing device, utilize the instrument resources to optimize efficiency;
     an analytics engine comprising software instructions which, when executed by the computing device, monitor realtime data output from the instrument resource sensors or the sample chamber sensors and initiate a calibration operation to update the model when a variance condition is detected in the data output; and
     an execution engine comprising software instructions which, when executed by the computing device, process the updated instrument workflow program and provide operating instructions to the instrument resources or the sample chambers.

2. The system of claim 1, wherein the software components further comprise:
   a machine learning engine comprising software instructions which, when executed by the computing device,

40 train the analytics engine to further improve the updated instrument workflow program.

3. The system of claim 1, wherein the one or more instrument resources comprises a pump, a nest, a needle, or a receptacle.

4. The system of claim 1, wherein the one or more sample chambers comprises an incubator, a well plate, or a tube.

5. The system of claim 1, wherein the one or more instrument resources and the one or more sample chambers are housed within a housing.

6. The system of claim 1, wherein the variance condition includes an alarm from the sensors, a warning of low material detected by the sensors, a result of a periodic image analysis, an end of workflow step notification, or a user input.

7. A method for dynamically updating an instrument system workflow, comprising:
   creating an instrument workflow program comprising software instructions which, when executed by a computing device, operate an instrument resource and a sample chamber housed in an instrument system;
   acquiring data from sensors monitoring the instrument resource or the sample chamber;
   updating a model of the instrument system in response to detecting a variance condition in the acquired data;
   generating an updated instrument workflow program utilizing the updated model, the updated workflow program comprising software instructions which, when executed by the computing device, utilize the instrument resource to optimize efficiency; and
   providing operating instructions to the instrument resource or the sample chamber based on the updated instrument workflow program.

8. The method of claim 7, further comprising:
   improving the updated model utilizing machine learning; and
   generating the updated instrument workflow program utilizing the updated model.

9. The method of claim 7, wherein the instrument resource comprises a pump, a nest, a needle, or a receptacle.

10. The method of claim 7, wherein the sample chamber comprises an incubator, a well plate, or a tube.

11. The method of claim 7, wherein the instrument resource, the sample chamber, or the sensors thereof are communicatively coupled to the computing device via a network connection.

12. The method of claim 7, wherein the instrument system comprises the computing device that is communicatively coupled to the instrument resource, the sample chamber, or the sensors thereof.

13. The method of claim 7, wherein updating the model includes updating the model periodically.

14. The method of claim 7, wherein the variance condition includes an alarm from the sensors, a warning of low material detected by the sensors, a result of a periodic image analysis, an end of workflow step notification, or a user input.

15. A non-transitory computer-readable storage medium storing thereon a computer program which, when executed by a computing device, performs a method for dynamically updating an instrument system workflow, the method comprising:
   creating an instrument workflow program comprising operating instructions for an instrument resource and a sample chamber comprising hardware components of an instrument system;

acquiring data from sensors monitoring the instrument resource or the sample chamber;

updating a model of the instrument system in response to detecting a variance condition in the acquired data;

generating an updated instrument workflow program utilizing the updated model, the optimized instrument workflow comprising software instructions which, when executed by the computing device, utilize the instrument resource to optimize efficiency; and providing operating instructions to the instrument resource or the sample chamber based on the updated instrument workflow program.

16. The non-transitory computer-readable storage medium of claim 15, wherein the method further comprises:

improving the updated model utilizing machine learning; and generating the updated instrument workflow program utilizing the improved updated model.

17. The non-transitory computer-readable storage medium of claim 15, wherein the instrument resource comprises a pump, a nest, a needle, or a receptacle.

18. The non-transitory computer-readable storage medium of claim 15, wherein the sample chamber comprises an incubator, a well plate, or a tube.

19. The non-transitory computer-readable storage medium of claim 15, wherein the instrument resource, the sample chamber, or the sensors thereof are communicatively coupled to the computing device via a network connection.

20. The non-transitory computer-readable storage medium of claim 15, wherein the instrument system comprises the computing device that is communicatively coupled to the instrument resource, the sample chamber, or the sensors thereof.

21. The non-transitory computer-readable storage medium of claim 15, wherein updating the model includes updating the model periodically.

22. The non-transitory computer-readable storage medium of claim 15, wherein the variance condition includes an alarm from the sensors, a warning of low material detected by the sensors, a result of a periodic image analysis, an end of workflow step notification, or a user input.

* * * * *